(12) United States Patent
Yasuno et al.

(10) Patent No.: US 12,367,548 B2
(45) Date of Patent: Jul. 22, 2025

(54) MEASUREMENT SIGNAL PROCESSING DEVICE, MEASUREMENT SIGNAL PROCESSING METHOD, AND PROGRAM

(71) Applicant: University of Tsukuba, Ibaraki (JP)

(72) Inventors: Yoshiaki Yasuno, Tsukuba (JP); Thitiya Seesan, Tsukuba (JP)

(73) Assignee: UNIVERSITY OF TSUKUBA, Tsukuba (JP)

( * ) Notice: Subject to any disclaimer, the term of this patent is extended or adjusted under 35 U.S.C. 154(b) by 399 days.

(21) Appl. No.: 17/916,032

(22) PCT Filed: Apr. 6, 2021

(86) PCT No.: PCT/JP2021/014585
§ 371 (c)(1),
(2) Date: Sep. 30, 2022

(87) PCT Pub. No.: WO2021/206076
PCT Pub. Date: Oct. 14, 2021

(65) Prior Publication Data
US 2023/0169627 A1     Jun. 1, 2023

(30) Foreign Application Priority Data

Apr. 10, 2020   (JP) ................................ 2020-070913

(51) Int. Cl.
  *G06T 3/4053*   (2024.01)
  *G06N 3/02*     (2006.01)
(52) U.S. Cl.
  CPC ............. *G06T 3/4053* (2013.01); *G06N 3/02* (2013.01); *G06T 2207/20084* (2013.01)
(58) Field of Classification Search
  None
  See application file for complete search history.

(56) References Cited

U.S. PATENT DOCUMENTS

2019/0110753 A1\*  4/2019  Zhang ................ A61B 3/0025
2019/0286632 A1\*  9/2019  Okuyama ........... G06F 16/2462
(Continued)

FOREIGN PATENT DOCUMENTS

| JP | 9-305567 A | 11/1997 | |
|---|---|---|---|
| JP | 2019159864 A | \* 9/2019 | .......... G05B 13/042 |
| JP | 2020-16992 A | 1/2020 | |
| JP | 2020-508536 A | 3/2020 | |

(Continued)

OTHER PUBLICATIONS

International Search Report and Written Opinion mailed on Jun. 29, 2021, received for PCT Application PCT/JP2021/014585, filed on Apr. 6, 2021, 11 pages including English Translation.
(Continued)

*Primary Examiner* — Jiangeng Sun
(74) *Attorney, Agent, or Firm* — XSENSUS LLP

(57) ABSTRACT

A model learning unit determines a model parameter for calculating an estimated value for each of a plurality of training sets, each including a measurement signal and at least one type of predetermined characteristic value indicating characteristics of the measurement signal as a target value, to minimize a difference between the estimated value calculated for the measurement signal using a predetermined mathematical model and the target value is minimized, determines characteristic value sets, each being a set of a plurality of types of characteristic values indicating characteristics of the measurement signal including the target value, with which, for each target value, the target value is common to a plurality of characteristic value sets, and generates, for each of the characteristic value sets, each of the plurality of training sets including the target value and a measurement signal having characteristics indicated by the plurality of types of characteristic values.

14 Claims, 9 Drawing Sheets

(56) References Cited

U.S. PATENT DOCUMENTS

2020/0003682 A1* 1/2020 Frenkel ............... G01N 23/083
2021/0089870 A1* 3/2021 Arik ..................... G06V 10/82
2021/0090253 A1* 3/2021 Ellis ..................... H04N 23/56

FOREIGN PATENT DOCUMENTS

JP          2020-57112 A      4/2020
JP         2020057112 A  *   4/2020
WO     WO-2018155898 A1 *   8/2018  ............ G06N 20/00

OTHER PUBLICATIONS

Hillman et al., "Correlation of static speckle with sample properties inoptical coherence tomography", Optics Letters, vol. 31, No. 2, Jan. 15, 2006, pp. 190-192.
Kurokawa et al., "In-plane and out-of-plane tissue microdisplacement measurement by correlation coefficients of optical coherence tomography", Optics Letters, vol. 40, No. 9, May 1, 2015, pp. 2153-2156.
Photiou et al., "Comparison of classification methods of Barret's and dysplasia in the esophagus from in vivo optical coherence tomography images", Proceedings of SPIE, vol. 11228, Feb. 21, 2020, pp. 1122820-1-1122820-4.
Seesan et al., "Intensity-invariant scatterer density estimation for optical coherence tomography using deep convolutional neural network", Proceedingsof SPIE, vol. 11521, Jun. 15, 2020, 115210Q-1-115210Q-3.
Japanese Office Action issued Jul. 30, 2024, in corresponding Japanese Patent Application No. 2022-514077, 7pp.

* cited by examiner

FIG. 5

| LAYER | TYPE | NUMBER OF KERNELS | KERNEL SIZE | STRIDE | ACTIVATION FUNCTION | AXIS |
|---|---|---|---|---|---|---|
| 0 | INPUT | 1 | 32x32x32 | - | - | - |
| 1 | CONVOLUTIONAL | 20 | 32x32x32 | - | ReLU | - |
| 2 | CONVOLUTIONAL | 20 | 32x32x32 | - | ReLU | - |
| 3 | NORMALIZATION | - | - | - | - | -1 |
| 4 | POOLING | - | - | 2 | - | - |
| 5 | CONVOLUTIONAL | 40 | 16x16x16 | - | ReLU | - |
| 6 | CONVOLUTIONAL | 40 | 16x16x16 | - | ReLU | - |
| 7 | NORMALIZATION | - | - | - | - | -1 |
| 8 | POOLING | - | - | 2 | - | - |
| 9 | CONVOLUTIONAL | 60 | 8x8x8 | - | ReLU | - |
| 10 | CONVOLUTIONAL | 60 | 8x8x8 | - | ReLU | - |
| 11 | NORMALIZATION | - | - | - | - | -1 |
| 12 | POOLING | - | - | 2 | - | - |
| 13 | CONVOLUTIONAL | 80 | 4x4x4 | - | ReLU | - |
| 14 | CONVOLUTIONAL | 80 | 4x4x4 | - | ReLU | - |
| 15 | NORMALIZATION | - | - | - | - | -1 |
| 16 | FLATTENING | 5120 | - | - | - | - |
| 17 | FULLY CONNECTED | 128 | - | - | ReLU | - |
| 18 | FULLY CONNECTED | 1 | - | - | - | - |

FIG. 6

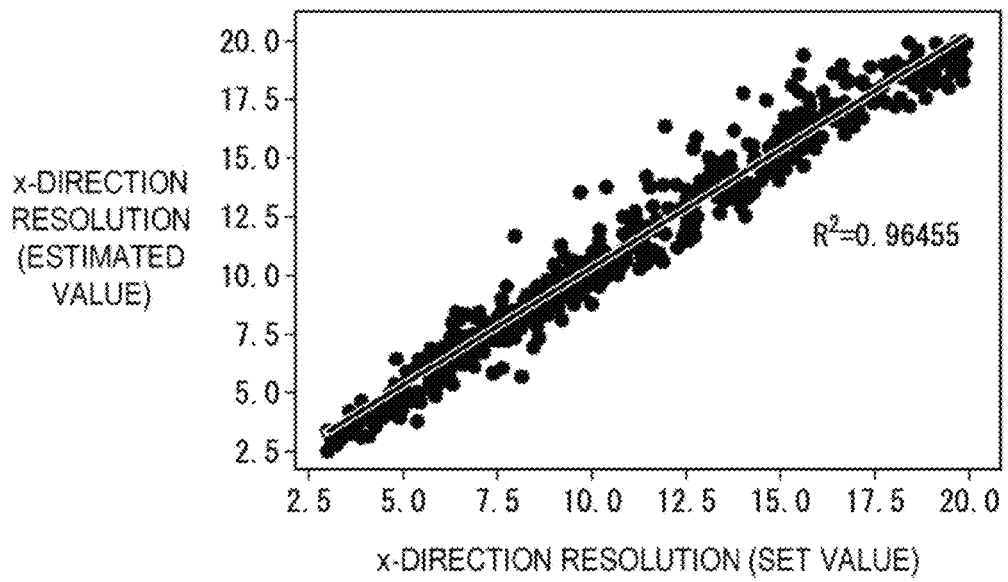

MEASUREMENT SIGNAL PROCESSING DEVICE, MEASUREMENT SIGNAL PROCESSING METHOD, AND PROGRAM

CROSS-REFERENCE TO RELATED APPLICATIONS

The present application is based on PCT filing PCT/JP2021/014585, filed Apr. 6, 2021, which claims priority to Japanese Patent Applications No. 2020-070913, filed on Apr. 10, 2020, the entire contents of each are incorporated herein by reference.

TECHNICAL FIELD

The present invention relates to a measurement signal processing device, a measurement signal processing method, and a program. The present invention relates to, for example, a technique for analyzing signals acquired by optical coherence tomography to estimate various characteristics of a sample to be measured and a technique for software implementation.

BACKGROUND ART

Optical coherence tomography (OCT) is a technique for acquiring a tomographic image of a sample (mainly a living object) using coherence of light. OCT can acquire images showing not only the surface of a sample but also the internal structure with high spatial resolution. OCT is applied to medical imaging diagnosis, tissue evaluation of living objects, and the like and interest is sometimes directed to changes in tissues and changes in the density of scatterers in tissues such as cell nuclei. On the other hand, the intensity of an OCT signal is affected not only by the scatterer density but also by the morphology of tissues themselves, the depths of measurement sites, the intensities of probe light from the sample and a light source, the signal-to-noise ratio, the image resolution, and the like. Therefore, it has not been practical to estimate the scatterer density from an OCT signal. Thus, practical diagnosis and evaluation using the scatterer density have not yet been achieved.

CITATION LIST

Non-Patent Literature

Non-Patent Literature 1: Timothy R. Hillman, et al., "Correlation of static speckle with sample properties in optical coherence tomography," OPTICS LETTERS Vol. 31, No. 2, p. 190-192, Jan. 15, 2006

Non-Patent Literature 2: Kazuhiro Kurokawa, et al., "In-plane and out-of-plane tissue micro-displacement measurement by correlation coefficient of optical coherence tomography," OPTICS LETTERS Vol. 40, No. 9, p. 2153-2156, May 1, 2015

SUMMARY OF INVENTION

Technical Problem

On the other hand, a speckle pattern inevitably occurs in an OCT signal. Speckles are irregularly distributed patchy patterns formed by light reflected or diffused from a sample. A speckle pattern refers to a spatial distribution of such patterns. The speckle contrast depends on the number of scatterers within the range of a coherence volume of OCT probe light as described in Non-Patent Literature 1. The coherence volume is a volume in a three-dimensional space determined by the spatial resolution of OCT. This indicates that the scatterer density can be estimated from the speckle contrast if the spatial resolution of OCT is known. That is, it is conceivable to relatively and subjectively estimate the scatterer density from the OCT signal under the assumption that the stronger the OCT signal, the higher the scatterer density. However, the resolution of the sample cannot be known in advance because the spatial resolution of OCT varies depending on the structure of the sample itself, an aberration caused by an OCT device, and an aberration occurring between the OCT device and the sample. The intensity of the OCT signal is also affected by factors other than the scatterer density.

On the other hand, Non-Patent Literature 2 describes a method of analyzing a speckle pattern to estimate the resolution of a tissue used as a sample. This also indicates that the density of scatterers in a sample can be estimated by analyzing a speckle pattern. However, it has not been possible to obtain the scatterer density with sufficient accuracy because the speckle pattern is affected by various factors such as the signal-to-noise ratio and aberration of the OCT signal. For the same reason, it has been difficult or impossible to correctly estimate, from a measurement signal such as an OCT signal, not only the scatterer density but also characteristics of the measurement signal itself or characteristics of the sample to be measured reflected in the measurement signal.

The present invention has been made in view of the above points and it is an object of the present invention to provide a measurement signal processing device, a measurement signal processing method, and a program that can more correctly estimate a characteristic value indicating characteristics of a measurement signal.

Solution to Problem (1) The present invention has been made to solve the above problems and an aspect of the present invention is a measurement signal processing device including a model learning unit configured to determine a model parameter for calculating an estimated value for each of a plurality of training sets, each including a measurement signal and at least one type of predetermined characteristic value indicating characteristics of the measurement signal as a target value, to minimize a difference between the estimated value calculated for the measurement signal using a predetermined mathematical model and the target value, and a training data generation unit configured to determine characteristic value sets, each being a set of a plurality of types of characteristic values indicating characteristics of the measurement signal, each including the target value, such that, for each target value, the target value is common to a plurality of characteristic value sets and generate, for each of the characteristic value sets, each of the plurality of training sets including the target value and a measurement signal having characteristics indicated by the plurality of types of characteristic values.

(2) Another aspect of the present invention is the measurement signal processing device of (1), wherein the training data generation unit may be configured to determine a tissue structure of a sample to be measured based on at least one of the plurality of types of characteristic values, and generate the measurement signal for a wave incident on the sample based on the tissue structure.

(3) Another aspect of the present invention is the measurement signal processing device of (1) or (2), wherein the training data generation unit may be configured to determine a characteristic value within a predetermined value range for each of the plurality of types using a random number.

(4) Another aspect of the present invention is the measurement signal processing device of any one of (1) to (3), wherein the target value may include a scatterer density of a sample, and the plurality of types of characteristic values include an intensity or a signal-to-noise ratio of the measurement signal.

(5) Another aspect of the present invention is the measurement signal processing device of (4), wherein the training data generation unit may be configured to determine a tissue structure of the sample in which scatterers are distributed at the scatterer density.

(6) Another aspect of the present invention is the measurement signal processing device of (4) or (5), wherein the target value may further include a spatial resolution of a measurement system.

(7) Another aspect of the present invention is the measurement signal processing device of any one of (1) to (6), wherein the plurality of types of characteristic values may include a spatial resolution, an aberration coefficient, or a dispersion coefficient relating to chromatic dispersion in a measurement system.

(8) Another aspect of the present invention is the measurement signal processing device of any one of (1) to (7), wherein the mathematical model may include a neural network including an input layer that outputs a signal value for each observation point of the measurement signal, which has been input to the input layer, to a first intermediate layer, a plurality of intermediate layers, and an output layer that outputs an estimated value based on an output value received from a last intermediate layer, the plurality of intermediate layers may be formed by repeatedly stacking one or more convolutional layers, each of which outputs an arithmetic value obtained by performing convolution processing on an input value received from an immediately preceding layer to a next layer, a plurality of times, and one or more final layers including the output layer may be fully connected layers, each of which outputs arithmetic values obtained by performing convolution processing on all of a plurality of input values received from an immediately preceding layer using a smaller number of parameter sets than the number of the input values.

(9) Another aspect of the present invention is the measurement signal processing device of any one of (1) to (8), which may further include a characteristic estimation unit configured to calculate, for the measurement signal, an estimated value for the target value based on the mathematical model using the model parameter.

(10) Another aspect of the present invention is the measurement signal processing device of (9), further including an output processing unit, wherein the measurement signal may indicate a signal value for each observation point, the characteristic estimation unit may be configured to calculate the estimated value for each block including a plurality of observation points, and the output processing unit may be configured to transform the estimated value into a pixel value and output display data indicating the pixel value to a display unit.

(11) Another aspect of the present invention is a signal processing program for execution of a phase gradient calculation process of calculating a phase gradient in a plane intersecting the irradiation direction of light of an optical coherence tomography signal representing the state of a sample for each sample point arranged in the plane and a bulk phase error process of, for each of a plurality of paths from a starting point which is a sample point at which a bulk phase error has been determined to an ending point which is a sample point at which no bulk phase error has been determined, integrating the phase gradient for each sample point along the path to calculate path-specific phase errors at the ending point and combining the path-specific phase errors of the plurality of paths to determine a bulk phase error at the end point.

(12) Another aspect of the present invention is a measurement signal processing method for a measurement signal processing device, the method including a model learning step of determining a model parameter for calculating an estimated value for each of a plurality of training sets, each including a measurement signal and at least one type of predetermined characteristic value indicating characteristics of the measurement signal as a target value, to minimize a difference between the estimated value calculated for the measurement signal using a predetermined mathematical model and the target value is minimized, and a training data generation step of determining characteristic value sets, each being a set of a plurality of types of characteristic values indicating characteristics of the measurement signal, each including the target value, such that, for each target value, the target value is common to a plurality of characteristic value sets and generating, for each of the characteristic value sets, each of the plurality of training sets including the target value and a measurement signal having characteristics indicated by the plurality of types of characteristic values.

(13) Another aspect of the present invention is a program for causing a computer for a measurement signal processing device to perform a model learning process of determining a model parameter for calculating an estimated value for each of a plurality of training sets, each including a measurement signal and at least one type of predetermined characteristic value indicating characteristics of the measurement signal as a target value, to minimize a difference between the estimated value calculated for the measurement signal using a predetermined mathematical model and the target value, and a training data generation process of determining characteristic value sets, each being a set of a plurality of types of characteristic values indicating characteristics of the measurement signal, each including the target value, such that, for each target value, the target value is common to a plurality of characteristic value sets and generating, for each of the characteristic value sets, each of the plurality of training sets including the target value and a measurement signal having characteristics indicated by the plurality of types of characteristic values.

Advantageous Effects of Invention

According to this invention, characteristics of a measurement signal can be estimated more correctly. For example, the scatterer density of a tissue which is a sample to be measured can be estimated from an OCT signal with higher accuracy than before.

BRIEF DESCRIPTION OF DRAWINGS

FIG. 5 is a table showing an exemplary configuration of the mathematical model according to the present embodiment.

FIG. 6 is a diagram showing a first example of calculation of a target value.

DESCRIPTION OF EMBODIMENTS

Figure 1:
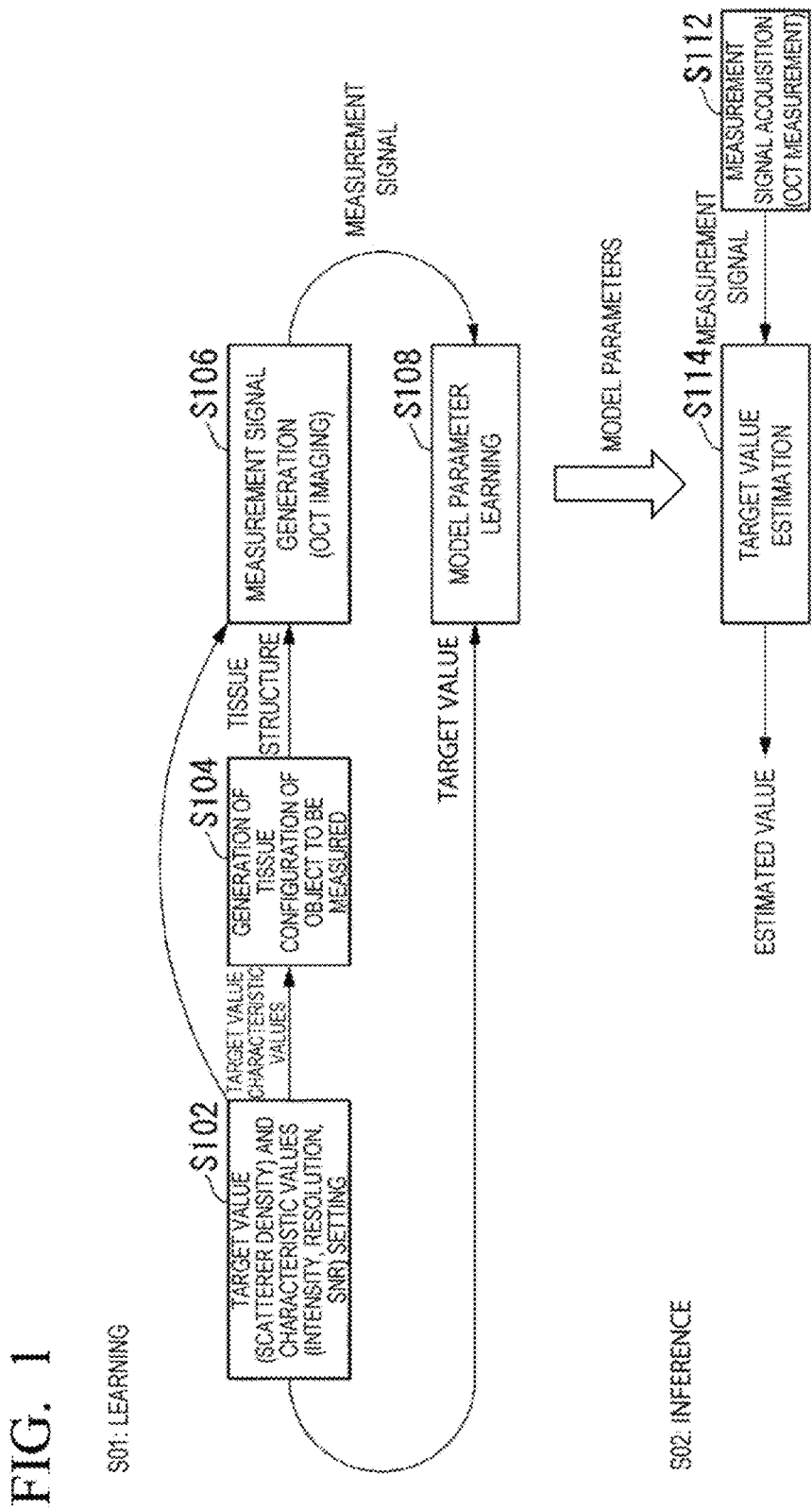
FIG. 1 is an explanatory diagram for explaining an outline of measurement signal processing according to the present embodiment.

Hereinafter, embodiments of the present invention will be described with reference to the drawings. First, an outline of the present embodiment will be described. FIG. 1 is an explanatory diagram for explaining an outline of measurement signal processing according to the present embodiment. It is assumed that a measurement signal processing device 100 according to the present embodiment can perform a learning step (S01) and an inference step (S02). The learning step S01 is a process of determining model parameters for estimating a predetermined target value among characteristic values representing the characteristics of an input measurement signal according to a predetermined mathematical model. The predetermined target value may be of one type or may be of a plurality of types. In the learning step S01, the measurement signal processing device 100 performs supervised learning. Supervised learning refers to recursive calculation of model parameters using sets, each including known input and output values, as training data (also called supervised data, learning data, or the like) to approximate estimated values calculated for the input values according to a mathematical model to the output values.

In the learning step S01, the measurement signal processing device 100 uses a measurement signal (for example, an OCT signal) and a target value as an input value and an output value, respectively. At least one type of predetermined characteristic value of the measurement signal (a scatterer density (the number of scatterers per unit volume (SPUV)) in the example illustrated in FIG. 1) is used as a target value. In the learning step S01, the measurement signal processing device 100 generates a plurality of sets of input and output values (hereinafter referred to as "training sets") and calculates model parameters with which the difference between the estimated value and the output value (hereinafter referred to as "model error") is minimized over a plurality of training sets. For example, a convolutional neural network (CNN) can be used as the mathematical model. Here, minimizing refers not only to absolutely minimizing but also to performing a calculation for estimating or searching for model parameters for the purpose of minimizing as much as possible. Thus, the model error does not necessarily decrease monotonically during the minimization process and may increase temporarily.

The learning step S01 according to the present embodiment includes, for example, the following steps S102 to S108.

(Step S102) The measurement signal processing device 100 sets a plurality of sets of a plurality of types of characteristic values indicating characteristics of a measurement signal as characteristic value sets. A characteristic value set includes a plurality of types of characteristic values and at least one type of predetermined characteristic value among the plurality of types of characteristic values is set as a target value in advance in the measurement signal processing device 100. That is, a plurality of types of target values may be included in a characteristic value set. A target value is determined to be common to a plurality of characteristic value sets. The number of types of characteristic values included in a characteristic value set is greater than the number of types of target values. When an SPUV is adopted as a type of characteristic value corresponding to a target value as exemplified in FIG. 1, a set of any, some, or all of the other types of characteristic values which are an intensity, a signal-to-noise ratio (SNR), a spatial resolution(s), an effective number of scatterers (ENS), and the like may be included in each characteristic value set.

(Step S104) The measurement signal processing device 100 determines, for each characteristic value set, a distribution of scatterers in the sample located in a predetermined observation area as a tissue configuration of the sample using the SPUV that has been set in step S102 as an example of the target value.

(Step S106) The measurement signal processing device 100 generates (simulates) a measurement signal in the observation area according to a predetermined signal model using the tissue structure determined for each characteristic value set and characteristic values of types different from the SPUV which is the target value. The measurement signal processing device 100 may generate an OCT signal as an example of the measurement signal or may generate OCT image data for visualizing the state of the sample based on the OCT signal (OCT imaging).

(Step S108) The measurement signal processing device 100 sets a set of the measurement signal generated for each characteristic value set and the target value (the SPUV for the example illustrated in FIG. 1) as a training set including an input value and an output value, respectively. The measurement signal processing device 100 calculates (learns) model parameters with which the model error between an estimated value calculated for the measurement signal according to the mathematical model and the output value is minimized over a plurality of training sets.

On the other hand, in the inference step S02, the measurement signal processing device 100 performs, for example, the processes of steps S112 and S114.

(Step S112) A measurement signal indicating the state of a sample in a predetermined observation area where the sample is placed is acquired through OCT measurement or the like.

(Step S114) The measurement signal processing device 100 calculates an estimated value for a target value (the SPUV in this example) using the model parameters obtained in the learning step S01 according to a predetermined mathematical model with the acquired measurement signal as an input value (target value estimation).

As described above, a plurality of characteristic value sets are determined for a target value, and using measurement signals generated based on characteristic value sets, each including a plurality of types of characteristic values, as input values, model parameters are determined to approximate an estimated value for the input value to the target value over the plurality of characteristic value sets. Using the determined model parameters, a value that approximates the target value is calculated as an estimated value for a measurement signal separately acquired as an input value. Thus, the measurement signal processing device 100 can determine a characteristic value robustly or invariantly to characteristic values of types different from the target value (such as, for example, the intensity and the resolutions) which are causes of variation in the measurement signal.

Measurement Signal Processing Device

Figure 2:
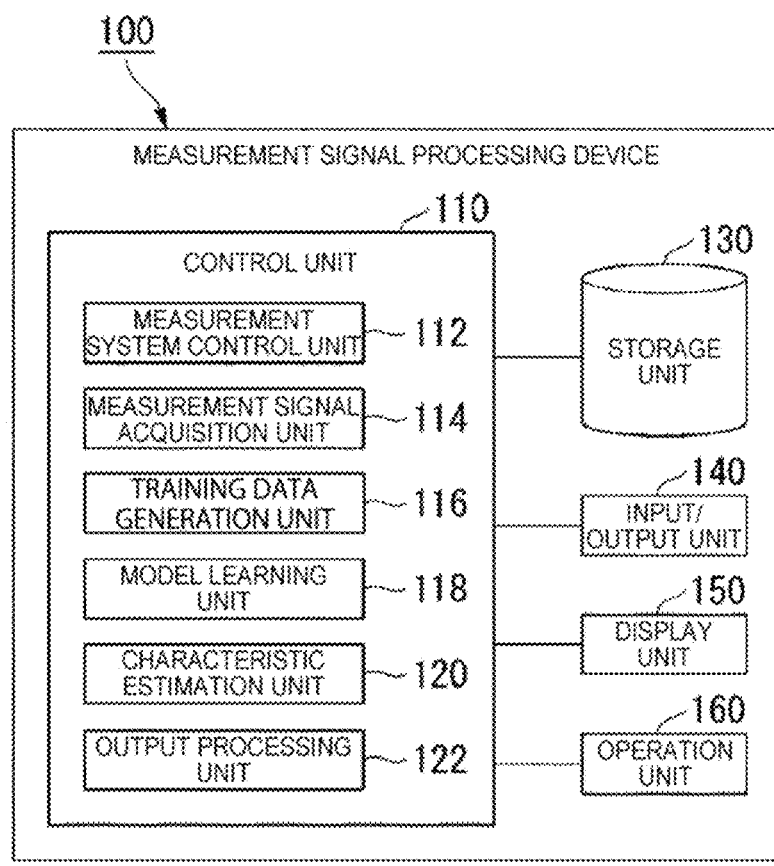
FIG. 2 is a block diagram illustrating an exemplary configuration of a measurement signal processing device according to the present embodiment.

Next, an exemplary configuration of the measurement signal processing device 100 according to the present embodiment will be described. FIG. 2 is a block diagram illustrating an exemplary configuration of the measurement signal processing device 100 according to the present embodiment.

The measurement signal processing device 100 includes a control unit 110, a storage unit 130, an input/output unit 140, a display unit 150, and an operation unit 160.

Some or all of the functions of control unit 110 are implemented, for example, as a computer including a processor such as a central processing unit (CPU). The processor reads a program that has been stored in the storage unit 130 in advance and performs a process instructed by commands written in the read program to implement the functions. In the present application, performing a process instructed by a command written in a program may be referred to as executing the program, execution of the program, or the like. A part or the entirety of the control unit 110 is not limited to general-purpose hardware such as a processor and may include dedicated hardware such as a large scale integration (LSI) and an application specific integrated circuit (ASIC).

The control unit 110 includes a measurement system control unit 112, a measurement signal acquisition unit 114, a training data generation unit 116, a model learning unit 118, a characteristic estimation unit 120, and an output processing unit 122.

The measurement system control unit 112 controls the range of the observation area of an object to be measured used as a sample installed in a measurement system. The measurement system control unit 112 sets the position or size of the observation area, for example, based on an operation signal received from the operation unit 160 and also controls the position of an observation point within the set observation area. For example, the measurement system control unit 112 scans observation points of a sample Sm by driving a driving mechanism that can change the positions of galvano mirrors 60a and 60b in an OCT system 1 (FIG. 3) that will be described later. The observation points of the sample Sm are scanned in a direction crossing the depth direction of the sample Sm (for example, a direction parallel to a front surface of the sample Sm).

The measurement signal acquisition unit 114 acquires a measurement signal indicating the state of the object to be measured from the measurement system. For example, the measurement signal acquisition unit 114 sequentially acquires a measurement signal from a spectrometer 70 in the OCT system 1. Based on the acquired measurement signal, the measurement signal acquisition unit 114 acquires a signal value indicating a distribution of the intensity of reflected light in the depth direction of the sample Sm for each of the observation points arranged at predetermined intervals. The measurement signal acquisition unit 114 repeats the process of acquiring the distribution of the intensity of reflected light for each observation point changed through the scanning. The acquired distribution of the intensity of reflected light is based on a distribution of the refractive index of the sample Sm in the depth direction. The measurement signal acquisition unit 114 can acquire an OCT signal representing the state of the sample Sm within the observation area as a measurement signal. The OCT signal has a signal value indicating, for each observation point, the complex amplitude of the intensity of interference light resulting from interference between reference light incident on the sample Sm and reflected light from the sample Sm. The measurement signal acquisition unit 114 stores the acquired measurement signal in the storage unit 130.

The training data generation unit 116 generates a training set for each characteristic value set. The training data generation unit 116 stores a series of data groups including training sets generated for characteristic value sets in the storage unit 130 as training data.

A training set includes a measurement signal as an input value and at least one type of predetermined characteristic value as a target value. First, the training data generation unit 116 generates a plurality of characteristic value sets. Each characteristic value set includes a plurality of types of characteristic values and at least one of the plurality of types of characteristic values is adopted as a target value. Here, the training data generation unit 116 determines characteristic value sets with which a target value is common to two or more characteristic value sets. The characteristic value sets differ in terms of the combination of types of characteristic values constituting the characteristic value set. In the present application, a characteristic value set and a characteristic value set in which some types of characteristic values are common with the former but other types of characteristic values differ from those of the former are distinguished as separate characteristic value sets. For example, the training data generation unit 116 generates two characteristic value sets 1 and 2 which include an SPUV and an SNR as characteristic values with the SPUV as a target value, the characteristic value set 1 having an SPUV of $0.01/\mu m^3$ and an SNR of 10 dB and the characteristic value set 2 having an SPUV of $0.01/\mu m^3$ and an SNR of 20 dB, as different characteristic value sets although they are common in that the SPUV is $0.01/\mu m^3$. When each target value is a set of characteristic values including a plurality of types of characteristic values, the training data generation unit 116 also distinguishes target values that differ in at least one type of characteristic value as different target values. In general, the training data generation unit 116 sets a plurality of target values. That is, the total number of generated characteristic value sets is the sum of the numbers of characteristic value sets set for the target values. Thus, the number of training sets (the number of sets) used to generate a set of model parameters is equal to the number of characteristic value sets, which is the sum of the number of characteristic value sets with a common target value (which is at least two) over the plurality of target values.

Each characteristic value can be either a scalar or a vector. For example, the SPUV, the ENS, the intensity, and the SNR are scalars. On the other hand, the resolutions may be treated as a vector having the same number of dimensions as the observation area or may be treated as individual independent scalars. For example, the resolutions in the three-dimensional observation area may be treated as a three-dimensional vector which has an x-direction resolution, a y-direction resolution, and a z-direction resolution as elements and the x-direction resolution, the y-direction resolution, and the z-direction resolution may be treated as separate scalars.

Here, the x-, y-, and z-directions are the directions of coordinate axes orthogonal to each other in a three-dimensional orthogonal coordinate system. The z-direction is the depth direction of the sample, and the x- and y-directions are the directions orthogonal to each other in a plane orthogonal to the z-direction. The process of determining such a series of characteristic value sets corresponds to the process of step S102 described above.

In setting the characteristic value sets, the training data generation unit 116 determines a plurality of values within a predetermined value range that can be taken for each type of characteristic value. The training data generation unit 116 determines, for example, three or more characteristic values distributed at equal intervals within a preset value range for each type. The training data generation unit 116 may also generate pseudorandom numbers that are uniformly distributed within a predetermined value range (hereinafter referred to as uniform random numbers) using a predetermined algebraic method and determine, as characteristic values, values obtained by scaling the generated pseudorandom numbers to cause the pseudorandom numbers to fall within a value range corresponding to the type of the characteristic values. For example, a method such as a linear congruential method or an M-sequence method can be used as the algebraic method. For a characteristic value that is a vector, the training data generation unit 116 individually determines a value for each element of the vector. In general, the range of a characteristic value may differ depending on the type of the characteristic. Here, a common value range may be set for element values or characteristic values of the same type, like for those of the x-direction resolution and the y-direction resolution. The training data generation unit 116 may be allowed to set the type and value range of each characteristic value to be processed, for example, based on an operation signal received from the operation unit 160.

Using some or all of the characteristic values in each characteristic value set, the training data generation unit 116 generates a measurement signal having characteristics represented by the characteristic values according to a predetermined propagation model for incident waves. The process of determining a scatterer distribution exemplified below corresponds to the process of step S104 and the process of determining an OCT speckle pattern as an example of the measurement signal from the scatterer distribution corresponds to the process of step S106.

Assuming the case where characteristic values constituting a characteristic value set include an SPUV as an example, the training data generation unit 116 generates a tissue structure in which scatterers are stochastically distributed at a determined SPUV within a predetermined observation area. More specifically, when the observation area is a three-dimensional area having a rectangular parallelepiped shape, the training data generation unit 116 multiplies the determined SPUV by the number of observation points within an area occupied by a sample located in the observation area to calculate the number of scatterers. The area occupied by the sample is preset. When it is assumed that the sample occupies the entire observation area, the training data generation unit 116 regards the number of observation points within the observation area as the number of observation points within the occupied area without considering the area occupied by the sample.

Then, the training data generation unit 116 sequentially generates uniform random numbers, scales a predetermined width, height, and depth of the observation area by every three generated random numbers to determine the coordinate values (x, y, z) of each scatterer in the observation area. The training data generation unit 116 repeats the process of determining the position of a scatterer the number of times corresponding to the number of scatterers. A distribution of scatterers within the observation area (hereinafter referred to as a scatterer distribution f(x, y, z)) is generated as a tissue structure.

Assuming the case where a characteristic value set includes spatial resolutions as an example, the training data generation unit 116 determines a point spread function (PSF) corresponding to the spatial resolutions. For example, the training data generation unit 116 determines, as the PSF(x, y, z), a three-dimensional normal distribution having x-, y-, and z-direction resolutions as standard deviations in the x-, y-, and z-directions, respectively, as shown in equation (1). Then, the training data generation unit 116 convolves the scatterer distribution f(x, y, z) with the point spread function PSF(x, y, z) to determine an OCT speckle pattern O(x, y, z) as shown in equation (2). The OCT speckle pattern is an OCT signal that can be observed as incident light is scattered by scatterers. In equation (1), $\sigma_x$, $\sigma_y$, and $\sigma_z$ represent standard deviations in the x-, y-, and z-directions, respectively.

[Math. 1]
$$PSF(x, y, z) \approx \exp\left(-\frac{x^2}{2\sigma_x^2} - \frac{y^2}{2\sigma_y^2} - \frac{z^2}{2\sigma_z^2}\right) \quad (1)$$

[Math. 2]
$$O(x, y, z) = F(x, y, z) * PSF(x, y, z) \quad (2)$$

Assuming the case where a characteristic value set includes an intensity as an example, the training data generation unit 116 scales a signal value for each observation point in the above OCT speckle pattern O(x, y, z) which is a measurement signal, for example, by multiplying the signal value by a constant proportional to the intensity. The training data generation unit 116 updates data indicating the signal value for each observation point with that after scaling as a new OCT speckle pattern (x, y, z).

Assuming the case where a characteristic value set includes an SNR as an example, the training data generation unit 116 adjusts a signal value for each observation point in the OCT speckle pattern O(x, y, z) which is a measurement signal, for example, by adding a noise component to the signal value. When determining noise component values, the training data generation unit 116 sequentially generates pseudorandom numbers whose distribution is a complex normal distribution and multiplies each generated random number by a gain to determine the noise component value for each observation point. The training data generation unit 116 determines the gain by which each noise component value is to be multiplied to achieve a result of the SNR being the ratio of the sum of squares of the absolute values of signal values to the sum of squares of the absolute values of noise component values in the observation area. When a measurement signal has been scaled, the training data generation unit 116 uses the scaled measurement signal as a target to which noise component values are to be added.

A plurality of types of characteristic values may have a dependent relationship. In that case, even if a certain type of characteristic value has not been set, the training data generation unit 116 may derive that type of characteristic value from another type of characteristic value. The training data generation unit 116 may or may not use the derived characteristic value as a target value. For example, the training data generation unit 116 may determine an SPUV by dividing an ENS that has been set by a coherence volume which is the product of spatial resolutions in the x-, y-, and z-directions. Conversely, the training data generation unit 116 may determine an ENS by multiplying an SPUV by a coherence volume which is the product of spatial resolutions in the x-, y-, and z-directions. The training data generation unit 116 may also determine the cube root of a volume obtained by dividing the ENS by the SPUV and the ratio of the spatial resolution in the z-direction to the spatial resolution in the x-y direction as each of an x-direction spatial resolution and a y-direction spatial resolution and then multiply the x-direction spatial resolution by the ratio of the spatial resolutions to determine a z-direction spatial resolution. The training data generation unit 116 may determine an SNR that is proportional to the intensity of a signal component, assuming that a noise level, that is, the sum of squares of noise component values within the observation area, is a constant value and may also add a signal component value scaled by the intensity and a noise component value together to calculate a signal value for each observation point. The SNR is given by the ratio of the sum of squares of the absolute values of signal values to the sum of squares of the absolute values of noise component values as described above.

Although the above description refers to the case where an OCT speckle pattern in an observation area in a three-dimensional space is determined as a measurement signal as an example, an OCT speckle pattern in an observation area in a two-dimensional space can be determined as a measurement signal using the same method. In that case, one of the x, y, and z coordinates may be omitted. For example, a point spread function PSF(x, y) and an OCT speckle pattern O(x, y) in a two-dimensional space such as the sample surface are given by equations (3) and (4), respectively, with the z coordinate omitted.

[Math. 3]
$$PSF(x, y) \approx \exp\left(-\frac{x^2}{2\sigma_x^2} - \frac{y^2}{2\sigma_y^2}\right) \quad (3)$$

[Math. 4]
$$O(x, y) = F(x, y) * PSF(x, y) \quad (4)$$

The model learning unit 118 reads training data from the storage unit 130 and determines a set of model parameters using a series of multiple training sets included in the read training data. The process of determining the model parameters corresponds to the process of step S108 described above. A model parameter refers to one or a plurality of parameters used in calculations according to a mathematical model and is sometimes called a parameter set or hyperparameter. The model learning unit 118 sets a measurement signal in each training set included in the training data as an input value to the mathematical model. The model learning unit 118 calculates model parameters with which a model error between an estimated value calculated as an output value for the measurement signal according to the mathematical model and the target value is minimized over the entirety of the series of training data. For example, a mean-square-error (MSE) can be used as a loss function that is an index indicating the magnitude of the model error. The MSE is a simple average of the squared differences between a target value $c_i$ and an estimated value $c_i^p$ over N samples i as shown in equation (5). The MSE is an index which indicates, as its value decreases, a smaller model error, that is, a higher degree of approximation of the estimated value to the target value. The model learning unit 118 repeats, for example, the process of recursively updating the model parameters using the steepest descent method until the MSE becomes equal to or less than a predetermined determination threshold. The model learning unit 118 stores model parameter data indicating the determined model parameters in the storage unit 130. An example of the mathematical model according to the present embodiment will be described later.

[Math. 5]
$$MSE = \sum_{i=1}^{N} \frac{(c_i - c_i^p)}{N} \quad (5)$$

The characteristic estimation unit 120 reads the model parameter data stored by the model learning unit 118 and the measurement signal stored by the measurement signal acquisition unit 114 from the storage unit 130. The process of acquiring the measurement signal corresponds to the process of step S112 described above. The characteristic estimation unit 120 calculates an estimated value for the target value, which is to be calculated, as an output value for the read measurement signal according to the above mathematical model using model parameters indicated by the read model parameter data. The process of calculating the estimated value corresponds to the process of step S114 described above. The characteristic estimation unit 120 stores the calculated estimated value in the storage unit 130 in association with the measurement signal.

The output processing unit 122 controls output of various data based on an operation signal received from the operation unit 160. The operation signal indicates, for example, whether to display the OCT image or whether to display the target value. When an operation signal indicating display of the OCT image has been input, the output processing unit 122 reads a measurement signal acquired by the measurement signal acquisition unit 114 or the training data generation unit 116 from the storage unit 130, converts the absolute value of a complex amplitude which is a signal value for each observation point indicated by the measurement signal into a luminance value within a predetermined value range of a pixel corresponding to the observation point, and outputs output image data having the converted luminance value to a display unit 150 as display data. As a result, an OCT image based on the output image data is displayed on the display unit 150. The output processing unit 122 may select a measurement signal to be output based on an operation signal. When an operation signal for instructing display of the target value has been input, the output processing unit 122 reads an estimated value for the target value calculated by the characteristic estimation unit 120 from the storage unit 130 and outputs display data indicating the read estimated value to the display unit 150. The output processing unit 122 may display the estimated value on the display unit 150, superimposed on the OCT image that is based on the measurement signal used to calculate the estimated value.

The output processing unit 122 may read setting screen data for guiding the setting of the above setting values (such as, for example, the observation area, the target value, the types of characteristic values, and the value range) from the storage unit 130 and output the read setting screen data to the display unit 150 as display data. In that case, a setting screen based on the setting screen data is displayed on the display unit 150.

The storage unit 130 stores various data used for processing performed by the control unit 110 and various data acquired by the control unit 110 in addition to the above program. The storage unit 130 includes, for example, a non-volatile (non-temporary) storage medium such as a read only memory (ROM), a flash memory, or a hard disk drive (HDD). The storage unit 130 includes, for example, a volatile storage medium such as a random access memory (RAM) or a register.

The input/output unit 140 is connected to other devices and various data can be input and output wirelessly or by wire. The input/output unit 140 includes, for example, an input/output interface. The input/output unit 140 is connected to, for example, a peripheral device or the measurement system.

The display unit 150 displays display information such as images, characters, and symbols based on display data received from the control unit 110. The display unit 150 may include, for example, a liquid crystal display or an organic electroluminescence display.

The operation unit 160 may include members such as buttons, knobs, dials, a mouse, and a joystick that receive user operations and generate operation signals according to the received operations. The operation unit 160 outputs an acquired operation signal to the control unit 110. The operation unit 160 may be an input interface that receives an operation signal from another device (for example, a portable device such as a remote control) wirelessly or by wire.

OCT System

Figure 3:
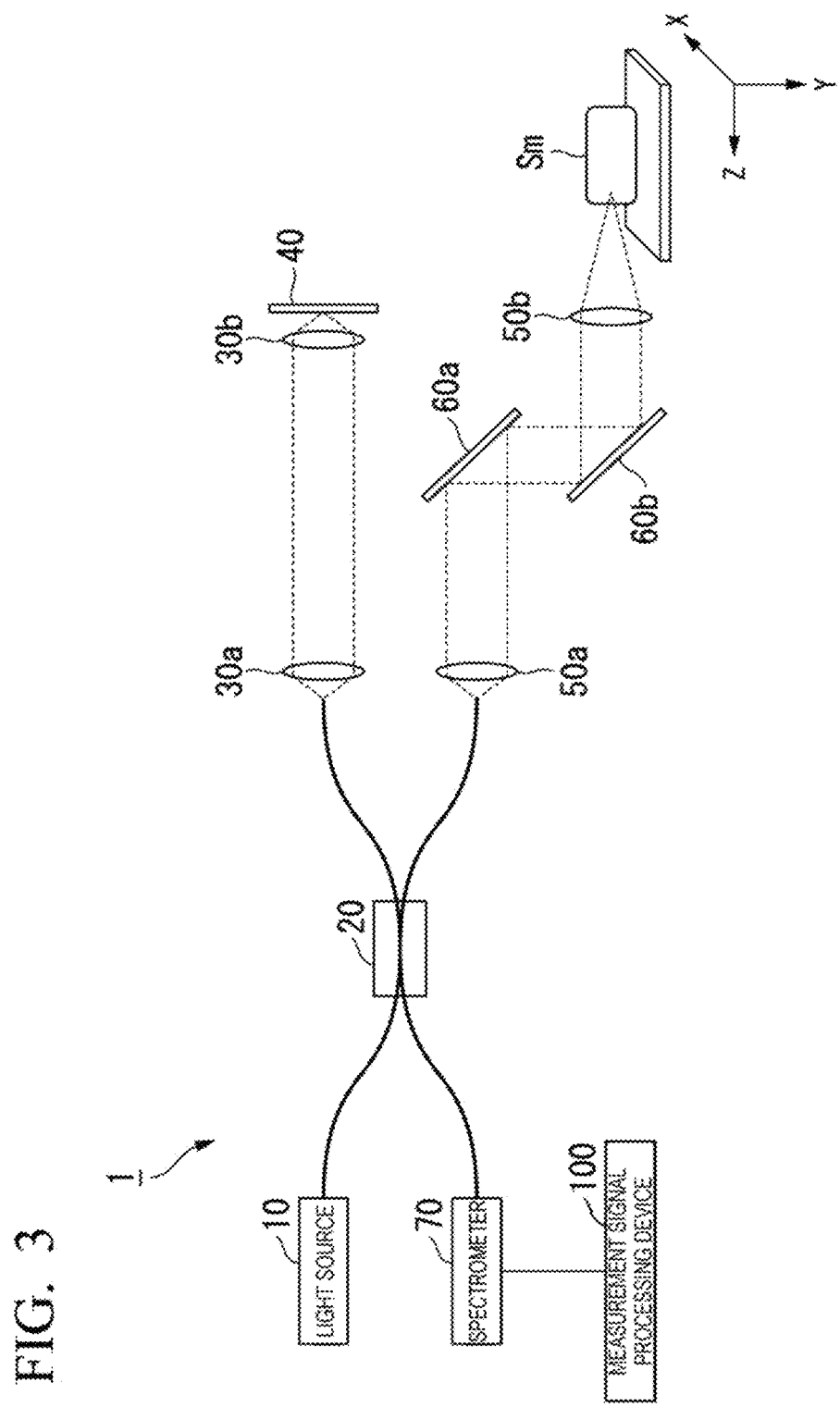
FIG. 3 is a configuration diagram illustrating an example of an OCT system according to the present embodiment.

Next, the OCT system 1 according to the present embodiment will be described. FIG. 3 is a configuration diagram illustrating an example of the OCT system 1 according to the present embodiment. The OCT system 1 is an observation system for observing the state of a sample using OCT.

The OCT system 1 irradiates a sample Sm with light, acquires interference light generated by interference between reflected light from the sample Sm and reference light reflected by a reference mirror 40, and acquires an OCT signal indicating the states of the front surface and the interior of the sample Sm from the acquired interference light as a measurement signal. The OCT system 1 converts the acquired measurement signal into an OCT image to visualize the acquired measurement signal.

The object to be observed, which is the sample Sm, may be, for example, a human or animal living object or a non-living object. A living object may be the fundus of an eye, a blood vessel, a tooth, a subcutaneous tissue, or the like. A non-living object may be any of an artificial structure such as an electronic part or a mechanical part, a natural structure such as a stone or a mineral, or a substance that does not have a specific shape.

The OCT system 1 includes a light source 10, a beam splitter 20, collimators 30a, 30b, 50a, and 50b, the reference mirror 40, the galvano mirrors 60a and 60b, the spectrometer 70, and the measurement signal processing device 100. Of these components, the beam splitter 20, the collimators 30a, 30b, 50a, and 50b, the reference mirror 40, the galvano mirrors 60a and 60b, and the spectrometer 70 constitute an optical system called an interferometer. The interferometer exemplified in FIG. 1 is a Michelson interferometer. More specifically, the light source 10, the spectrometer 70, the collimator 30a, and the collimator 50a are each connected to the beam splitter using an optical fiber. The OCT system 1 is, for example, Fourier-domain OCT (FD-OCT).

The light source 10 is a broadband light source such as an ultrashort pulse laser or a superluminescent diode (SLD). The light source 10 has, for example, near-infrared wavelengths (for example, 800 to 1000 nm) and emits low-coherence probe light. Light emitted from the light source 10 is guided inside the optical fiber and incident on the beam splitter 20. The beam splitter 20 splits the incident light into light guided toward the collimator 30a (hereinafter referred to as reference light) and light guided toward the collimator 50a (hereinafter referred to as measurement light). The beam splitter 20 is, for example, a cube beam splitter.

The collimator 30a converts the reference light guided from the beam splitter 20 into parallel light and emits the parallel light toward the collimator 30b.

The collimator 30b condenses the parallel light incident from the collimator 30a and emits the condensed reference light toward the reference mirror 40. The collimator 30b receives the reference light reflected by the reference mirror 40, converts it into parallel light, and emits the converted parallel light toward the collimator 30a. The collimator 30a condenses the parallel light incident from the collimator 30b and guides it toward the beam splitter 20.

On the other hand, the collimator 50a converts the measurement light guided from the beam splitter 20 into parallel light and emits the converted parallel light toward the galvano mirror 60a. On the surfaces of the galvano mirrors 60a and 60b, the parallel light incident from the collimator 50a is reflected and emitted toward the collimator 50b. The collimator 50b condenses the parallel light which is incident from the collimator 50a via the galvano mirrors 60a and 60b and irradiates the sample Sm with the condensed measurement light. The measurement light with which the sample Sm has been irradiated is reflected by a reflective surface of the sample Sm and incident on the collimator 50b. The reflective surface is not limited to, for example, a boundary surface between the sample Sm and the surrounding environment of the sample Sm (for example, air) and may be a boundary surface that separates materials or tissues having different refractive indices inside the sample Sm. Hereinafter, the light reflected by the reflective surface of the sample Sm and incident on the collimator 50b will be referred to as reflected light.

The collimator 50b emits the incident reflected light toward the galvano mirror 60b. The light is then reflected on the surfaces of the galvano mirrors 60b and 60a and emitted toward the collimator 50a. The collimator 50a condenses the parallel light which is incident from the collimator 50a via the galvano mirrors 60a and 60b and guides the condensed reflected light toward the beam splitter 20.

The beam splitter 20 guides the reference light reflected by the reference mirror 40 and the reflected light reflected by the sample Sm to the spectrometer 70 via an optical fiber.

The spectrometer 70 has a diffraction grating and a light receiving element inside. The diffraction grating spectrally separates the reference light and reflected light guided from the beam splitter 20. The spectrally separated reference light and reflected light interfere with each other to produce interference light. The light receiving element is arranged on an imaging surface which is irradiated with the interference light. The light receiving element detects the irradiated interference light and generates a measurement signal corresponding to the detected interference light. The light receiving element outputs the generated measurement signal to the measurement signal processing device 100. It is desirable that the interval between adjacent observation points in the observation area be equal to or less than the spatial resolution of the optical system.

Mathematical Model

Figure 4:
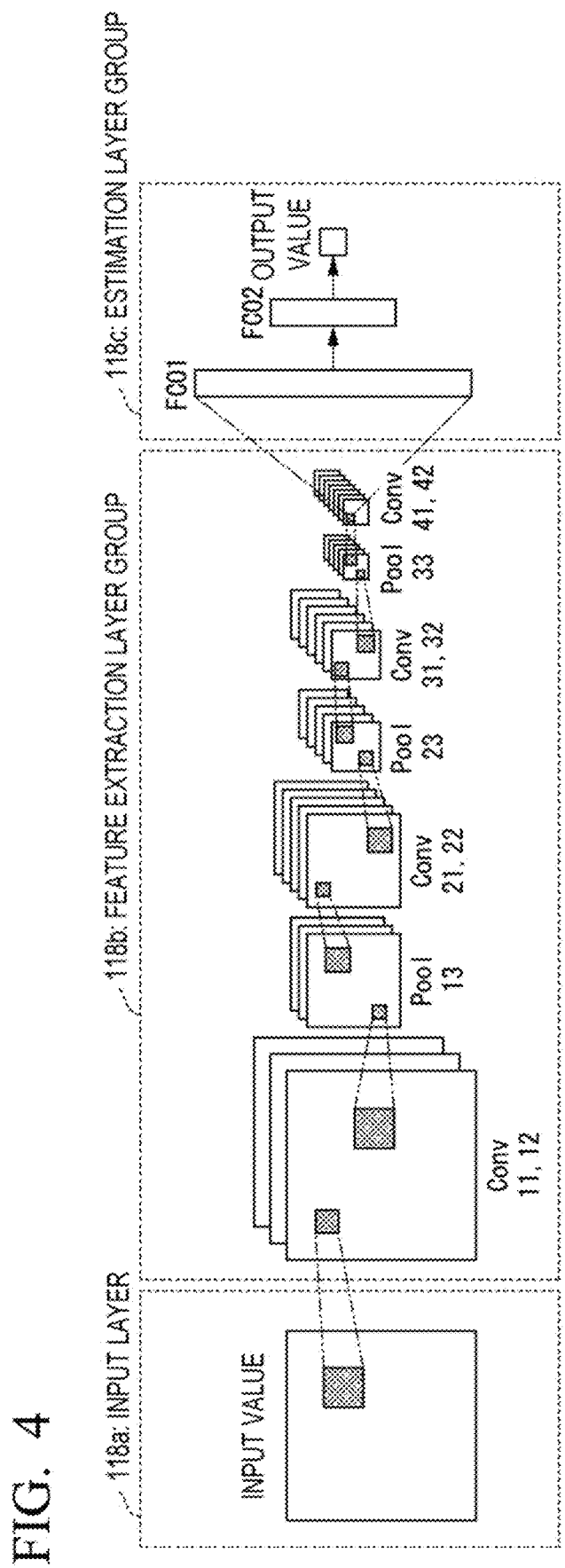
FIG. 4 is an explanatory diagram illustrating an example of a mathematical model according to the present embodiment.
Figure 7:
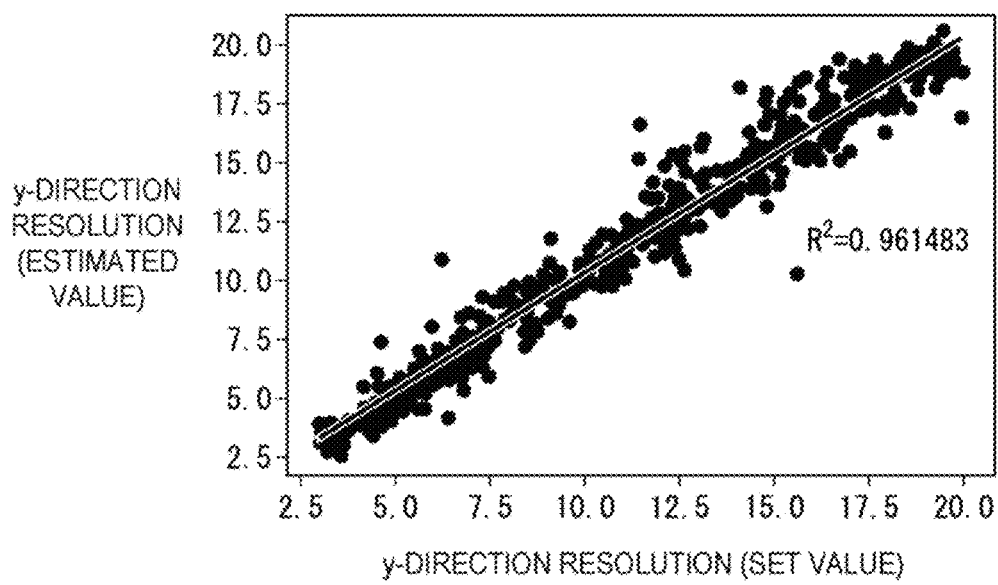
FIG. 7 is a diagram showing a second example of calculation of a target value.
Figure 8:
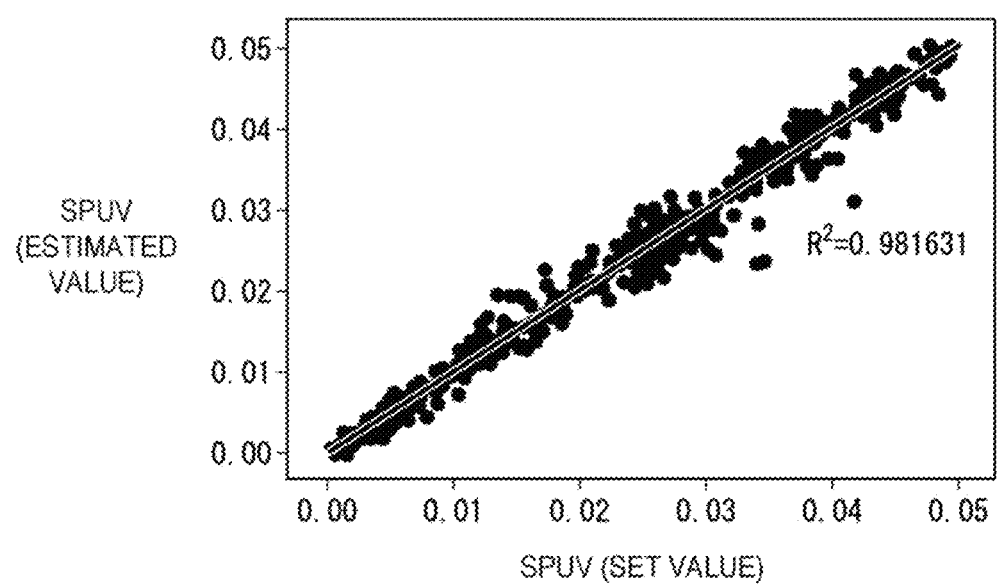
FIG. 8 is a diagram showing a third example of calculation of a target value.
Figure 9:
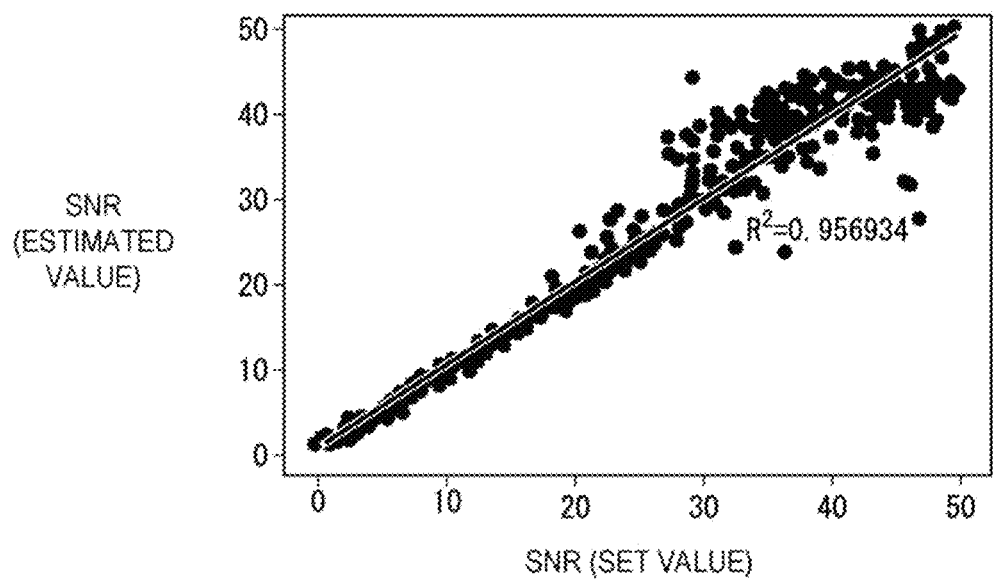
FIG. 9 is a diagram showing a fourth example of calculation of a target value.
Figure 10:
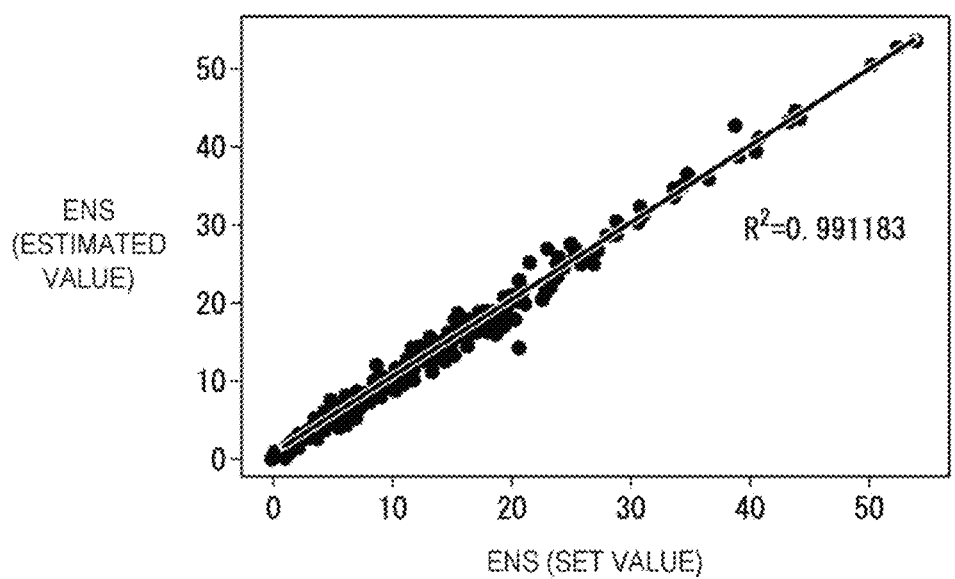
FIG. 10 is a diagram showing a fifth example of calculation of a target value.

Next, an example of a mathematical model according to the present embodiment will be described. FIG. 4 is an explanatory diagram illustrating an example of a mathematical model according to the present embodiment. FIG. 5 is a table showing a configuration of the mathematical model exemplified in FIG. 4. FIG. 5 shows the layer number, type, number of kernels, kernel size, stride, activation function, and axis of each layer in columns. Here, "-" indicates that there is no corresponding entry for a given type of layer.

The mathematical model illustrated in FIGS. 4 and 5 is a CNN. In the example illustrated in FIGS. 4 and 5, an input value to the CNN is a three-dimensional OCT signal, which is used to calculate a one-dimensional target value (scalar) from the CNN as an output value. One-dimensional characteristic values correspond to, for example, a diffuser density, a signal intensity, an ENS, an SNR, and the resolution of each direction (that is, the x, y, and z-direction resolutions).

A CNN is a type of artificial neural network and includes an input layer, a plurality of intermediate layers, and an output layer. The CNN exemplified in FIG. 4 includes an input layer 118a, a feature extraction layer group 118b, and an estimation layer group 118c. A 0th layer exemplified in FIG. 5 corresponds to the input layer 118a, 1st to 16th layers correspond to the feature extraction layer group 118b, and the 17th and 18th layers correspond to the estimation layer group 118c. The layers belonging to the feature extraction layer group 118b and the first layer of the estimation layer group 118c correspond to the intermediate layers and the last layer of the estimation layer group 118c corresponds to the output layer. Each layer has one or more nodes (also called neurons or the like). Each node outputs a function value of a predetermined function for an input value as an output value. Here, when a three-dimensional measurement signal is dealt with, the resolution takes a three-dimensional vector value. Therefore, a CNN having an output layer with three nodes may be used when the resolution is calculated as a three-dimensional output value.

The input layer 118a outputs a signal value for each observation point indicated by a measurement signal that has been received as an input value to a next layer. Each node of the input layer 118a receives a signal value of an observation point corresponding to that node and outputs the received signal value to a corresponding node of a next layer. "Number of kernels" in FIG. 5 indicates the number of kernels used for processing (for example, calculation) of each input value. A kernel refers to a processing unit for calculating an output value at a time. Kernels are also called filters. "Kernel size" indicates the number of input values used for processing performed once in the kernel. For example, it is shown that the 0th layer in FIG. 5 has a kernel having 32×32×32 nodes of the input layer 118a and an output value is given for an input value to each node.

The feature extraction layer group 118b calculates, from a multidimensional input value, extracted feature values indicating its features. In the example illustrated in FIG. 4, the feature extraction layer group 118b is formed by alternately stacking one or more convolutional layers and a pooling layer two or more times. More specifically, the feature extraction layer group 118b is formed by stacking two adjacent convolutional layers Conv11 and Conv12, one pooling layer Pool13, two convolutional layers Conv21 and Conv22, one pooling layer Pool23, two convolutional layers Conv31 and Conv32, one pooling layer Pool33, and convolutional layers Conv41 and Conv42 in that order. Here, one normalization layer is sandwiched between the second of each pair of convolutional layers and a next layer. The feature extraction layer group 118b includes a flattening layer as a final layer.

A convolutional layer is a layer that performs a convolution operation on each input value, which is input to each of a plurality of nodes of the layer from an immediately preceding layer, with each kernel to calculate a convolution value, calculates a function value of a predetermined activation function for a corrected value obtained by adding the calculated convolution value and a bias value together as an output value, and outputs the calculated output value to a next layer. In the convolution operation, one or a plurality of input values are input to each node from an immediately preceding layer and independent convolution coefficients are used for the input values. The convolution coefficients, bias values, and activation function parameters constitute a part of a set of model parameters.

For example, the numbers of kernels in the 1st and 2nd layers in FIG. 5 are set to 1 and 20, respectively. The kernel size of each of the 1st and 2nd layers is 32×32×32. The number of kernels being 20 indicates that there are 20 different convolution coefficients, output values corresponding to the 20 kernels are obtained for each node, and the obtained output values are input to corresponding nodes of a next layer. ReLU in the activation function field indicates that the activation function is a rectified linear unit. The rectified linear unit is a function that determines that an output value for an input value equal to or lower than a predetermined threshold value (for example, 0) is the predetermined threshold value and directly outputs an input value that exceeds the predetermined threshold value. Thus, this threshold value can also be a part of a set of model parameters. Whether it is necessary for a convolutional layer to reference input values from nodes of an immediately preceding layer and whether it is necessary for it to output the output values to nodes of a next layer can also be a part of a set of model parameters. Therefore, unlike fully connected layers that will be described later, each node of a convolutional layer does not necessarily connect to all nodes of an immediately preceding layer and receive input values from them and does not necessarily connect to all nodes of a next layer and output an output value to them.

A normalization layer is a layer that normalizes input values input to a plurality of nodes of the layer within a predetermined value range using a common normalization parameter (batch normalization) and outputs the normalized values as output values. A sign indicating the type and value range of a parameter as an axis used for normalization is set in the field of the axis of the 3rd layer in FIG. 5. "−1" set in this field is a sign indicating that output values from all nodes are normalized within a value range from 0 to 1 through multiplication using a common multiplication value.

A pooling layer is a layer having nodes, each of which determines a representative value from input values received from a plurality of nodes of an immediately preceding layer and outputs the determined representative value to a next layer as an output value. For example, a value that statistically represents the plurality of input values such as a maximum, an average, or a mode is used as the representative value. The number "2" set in the stride field of the 4th layer in FIG. 5 indicates the range of adjacent nodes in an immediately preceding layer from which input values are referenced by one node of the 4th layer. In the example shown in FIG. 5, 2×2×2 immediately preceding nodes that are spatially adjacent in the three-dimensional space are referenced. Thus, a pooling layer is a layer that reduces (downsamples) input values from an immediately preceding layer to lower dimensionality and provides the resulting output values to a next layer.

The estimation layer group 118c is a layer that calculates an estimated value from extracted feature values received from the feature extraction layer group 118b as an output value. The estimation layer group 118c is formed by stacking a flattening layer (in FIG. 5, but not shown in FIG. 4) and two fully connected layers FC01 and FC02. The flattening layer is a layer that unrolls input values of a multi-dimensional sample of three or more dimensions into output values of a two-dimensional sample. For example, the 16th layer of FIG. 5 receives element values of 80 three-dimensional arrays of 4×4×4 observation points normalized and output by the 15th layer as input values and linearly permutes the three dimensional arrays of a total of 5120 input values to convert them into a vector having element values of 5120 dimensions. Thus, the flattening layer does not perform any substantial arithmetic operations. A fully connected layer is a layer that performs a convolution operation on input values, which are input to a plurality of nodes of the layer from an immediately preceding layer, to calculate convolution values, calculates corrected arithmetic values obtained by adding the calculated convolution values and bias values together as output values, and outputs the calculated output values to a next layer. That is, a fully connected layer is a layer that outputs arithmetic values obtained by performing convolution processing on all of a plurality of input values received from an immediately preceding layer using a smaller number of parameter sets (kernels) than the number of the input values. A predetermined activation function may be set for each node of the fully connected layer and a function value of the predetermined activation function for a calculated correction value may be output to the next layer as an output value. In the 17th layer of FIG. 5, a rectified linear unit is set as an activation function for each of the 128 kernels and input values from 40 nodes of the 16th layer are referenced as input values to calculate an output value. In the 18th layer of FIG. 5, a convolution value obtained by performing a convolution operation on input values from 128 nodes of the 17th layer is calculated as an output value. Thus, in each fully connected layer, convolution coefficients, bias values, and activation function parameters constitute a part of a set of model parameters. One or more final layers including the output layer are fully connected layers and thus components significantly affecting a characteristic value which are given from an immediately preceding layer can be fully taken into account and the degree of freedom can be reduced to finally derive the characteristic value.

The number of CNN layers, the type of each layer, the number of nodes of each layer, and the like are not limited to those illustrated in FIGS. 4 and 5. The CNN according to the present embodiment only needs to have a configuration capable of calculating an estimated value for a predetermined target value as an output value for a measurement signal having signal values for a plurality of observation points as an input value. An estimated value is not limited to a one-dimensional scalar value as described above and can be a vector or matrix of two or more dimensions. For example, a characteristic value may be a three-dimensional resolution vector having an x-direction resolution, a y-direction resolution, and a z-direction resolution as elements. A measurement signal is not limited to a three-dimensional signal in which observation points are distributed in a three-dimensional space and may be a signal with lower dimensionality than a two-dimensional signal or a high-dimensional signal with four or more dimensions. It is preferable that the CNN according to the present embodiment include an intermediate layer constructed by sequentially stacking one or more convolutional layers and a pooling layer alternately and repeatedly in two or more cycles as exemplified in FIGS. 4 and 5. This is because the repetition of convolutional layers narrows down components that significantly affect a characteristic value. Pooling layers may be omitted in repeating the convolutional layers.

As described above, the characteristic estimation unit 120 uses a mathematical model such as a CNN to calculate an estimated value for each block of a plurality of adjacent observation points forming an OCT signal. Thus, an OCT signal that gives an OCT image of one frame usually corresponds to a plurality of blocks. Therefore, when an operation signal indicating display of a target value has been input, the output processing unit 122 may convert an estimated value calculated for each block into a luminance value within a predetermined value range of pixels corresponding to the block. The output processing unit 122 outputs display data indicating the converted luminance values to the display unit 150. As a result, the display unit 150 displays a target value image that expresses a distribution of target values for blocks using luminance.

Examples of Calculation of Characteristic Values

Next, examples of calculation of characteristic values that are calculated in the estimation step (S02) using the model parameters obtained by performing the learning step (S01) will be described. In the following calculation examples, a two-dimensional sample surface (an en-face surface) with 32×32 observation points was used as an observation area. Each characteristic value set includes an x-direction resolution, a y-direction resolution, an SPUV, and an SNR as characteristic values. An OCT speckle pattern in which scatterers are stochastically distributed at the SPUV and which has the set x-direction resolution, y-direction resolution, and SNR as its characteristics was used as a measurement signal. Then, the model learning unit 118 was caused to calculate model parameters of a CNN for calculating an estimated value for a target value using a plurality of pieces of training data, each including a measurement signal and one of an x-direction resolution, a y-direction resolution, an SPUV, and an SNR as a target value. That is, a total of four sets of model parameters for calculating estimated values of the x-direction resolution, the y-direction resolution, the SPUV, and the SNR were calculated from a common measurement signal given in each characteristic value set. Here, a value range of each of the x-direction resolution and the y-direction resolution was 3 to 20 µm, a value range of the SNR was 0 to 50 dB, and a value range of the SPUV was 0 to $0.0497/\mu m^2$. The characteristic values of each type were determined using uniform random numbers that achieved random distribution within their value range.

Training sets based on 50,000 characteristic value sets were used to calculate a set of model parameters. The 50,000 characteristic value sets included a plurality of characteristic value sets, each having a common target value (for example, an SPUV of $0.03/m^2$), and an OCT speckle pattern of 32×32 pixels was generated from each characteristic value set. The size of one pixel corresponds to approximately 1 µm to several µm, depending on the specifications of various devices and a method of scanning OCT signals. Then, the characteristic estimation unit 120 was caused to, given an OCT speckle pattern whose target values indicating its characteristics were known as a measurement signal, calculate an estimated value for each target value according to the CNN exemplified in FIG. 5 using each of the four sets of model parameters calculated by the model learning unit 118. Here, the characteristic estimation unit 120 used OCT speckle patterns other than those that the model learning unit 118 has used to calculate the model parameters.

FIGS. 6 to 10 are diagrams showing examples of calculation of target values. In each of FIGS. 6 to 10, the vertical axis indicates an estimated characteristic value and the horizontal axis indicates a set value for a characteristic value. Here, an OCT speckle pattern having signal values of a total of 32,768 points, which were 32×32×32 points in the width, height, and depth as respective dimensions in the x-, y-, and z-directions, was used as an input value. In FIGS. 6 to 10, "estimated value" indicates an estimated value for a target value as an output value calculated from a measurement signal using the model parameters and "set value" indicates a target value included in a characteristic value set used to calculate the model parameters. FIGS. 6, 7, 8, 9, and 10 illustrate respectively the x-direction resolution, the y-direction resolution, the SPUV, the SNR, and the ENS as a target value. It is shown that the set value and the estimated value are nearly equal for any of the x-direction resolution, the y-direction resolution, the SPUV, the SNR, or the ENS.

The respective coefficients of determination $R^2$ obtained by performing linear regression analysis on the distributions of estimated values for set values for the x-direction resolution, the y-direction resolution, the SPUV, the SNR, and the ENS were 0.965, 0.961, 0.981, 0.957, and 0.991, which are close to 1. In the linear regression analysis, it was assumed that a set value as an input value and an estimated value as an output value were the same. In general, the coefficient of determination $R^2$ indicates the degree of contribution of a variance determined by an input value to a variance of an output value and the closer it is to 1, the higher the accuracy of estimation by the model parameters. The calculation examples shown in FIGS. 6-10 show that model parameters that enable highly accurate estimation are obtained for all of the x-direction resolution, the y-direction resolution, the SPUV, the SNR, and the ENS. However, there is a slight difference in estimation accuracy depending on the type of the target value. For example, the respective coefficients of determination $R^2$ of the x-direction resolution and the y-direction resolution were 0.965 and 0.961 which are nearly equal, while the respective coefficients of determination $R^2$ for the SPUV and the ENS were 0.981 and 0.991, which are higher than the coefficients of determination $R^2$ for the resolutions. In particular for the ENS, it was found that the variance around the regression line was smaller than those of other estimated values and there was a tendency that the larger the absolute value of the ENS, the smaller the variance. This indicates that when the ENS is high, the influence of variations in a measurement signal due to an increase in the number of scatterers is more significant than that of variations in a measurement signal due to resolutions. On the other hand, regarding the SNR, it was found that the larger the absolute value of the SNR, the larger the variance. This indicates that when the SNR is high, factors other than noise such as calculation errors have a significant influence on the estimation accuracy of the SNR.

Although the examples shown in FIGS. 4 to 10 have been described with respect to the case where the training data generation unit 116 generates training sets, each including a type of characteristic value in each characteristic value set as a target value, and the model learning unit 118 generates model parameters using target values included in the training set as output values as an example, the present invention is not limited to this. The training data generation unit 116 may generate training sets, each including two or more types of characteristic values in each characteristic value set as target values. Thus, the model learning unit 118 can generate model parameters for simultaneously calculating two or more types of characteristic values as estimated values that are calculated from a measurement signal as an input value. For example, an x-direction resolution, a y-direction resolution, and an SPUV may be included in a training set.

In verification examples described below, SPUVs estimated from OCT signals obtained from actual biological samples by using the OCT system 1 using model parameters learned under the above conditions were evaluated over a long period of time. Human breast cancer cell spheroids (of MCF-7 cell line) were used as biological samples. The diameters of biological samples were approximately 250 μm. The biological samples were cultured in a cultivation chamber from seeding under a carbon dioxide ($CO_2$) supply environment. The culture was then terminated and the biological samples were removed from the cultivation chamber and placed in a culture medium. The medium was not supplied with $CO_2$ and the temperature was 22° C. Then, OCT signals of the biological samples were acquired every two hours.

In acquiring OCT signals, swept source OCT (SS-OCT) was used and the center wavelength of the light source was 1.3 μm. SS-OCT corresponds to a type of FD-OCT. The A-scan speed of OCT signals was 50,000 lines per second. The spatial resolution in observation of OCT signals was 19 μm in the lateral direction (corresponding to any direction in the xy plane described above) and 14 μm in the depth direction (corresponding to the z-direction described above).

In the evaluation, a logarithmic intensity variance (LIV) was used in addition to an SPUV calculated from the acquired OCT signal. The LIV corresponds to the time variance of the logarithmic intensity of the OCT signal within a predetermined period of time (for example, 1 to 10 seconds). The LIV is used as an index value indicating the degree of dynamics of biological tissues.

Figure 11:
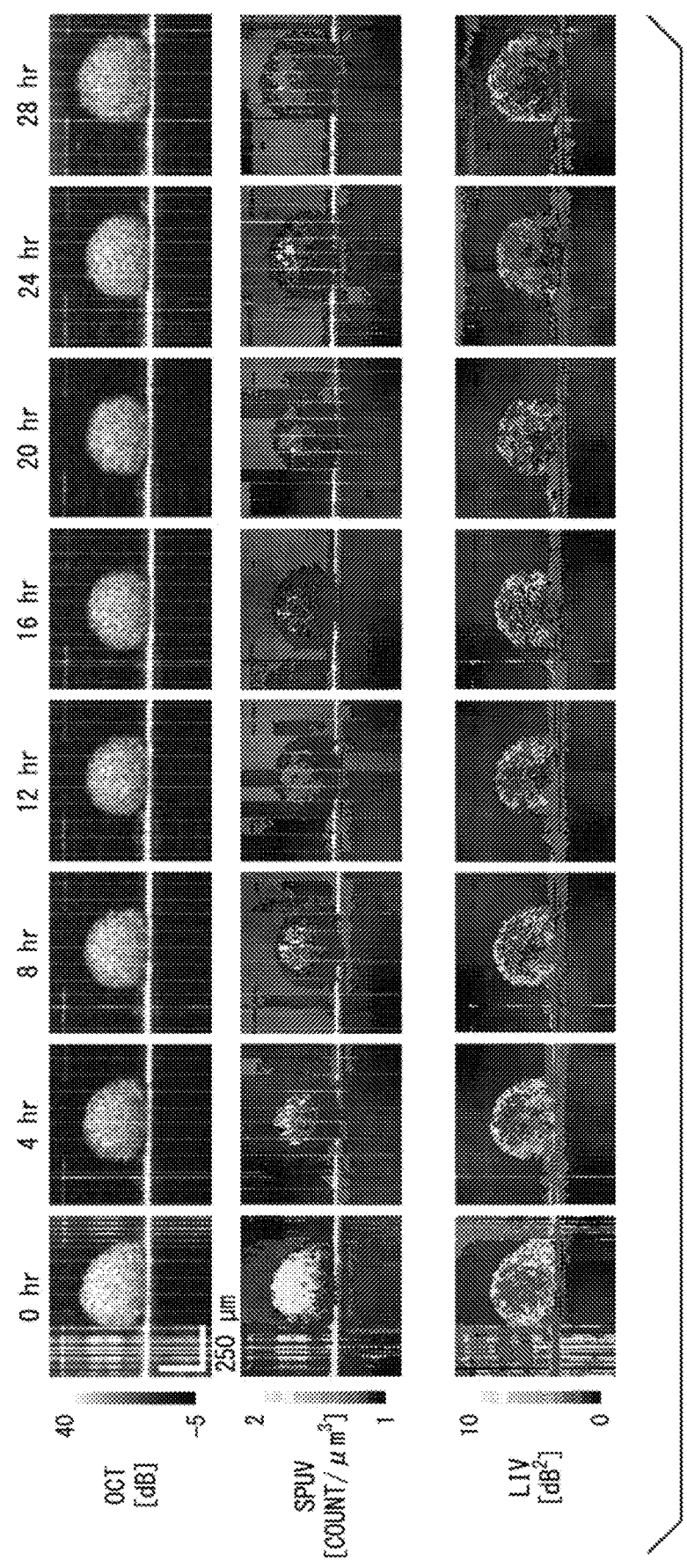
FIG. 11 is a diagram showing examples of observation of biological samples.

FIG. 11 is a diagram showing examples of observation of biological samples. FIG. 11 shows OCT, SPUV and LIV images in first, second, and third rows, respectively. Each image is based on OCT signals observed every 4 hours from the end of each culture. Each OCT image shows the OCT signal intensity for each observation point. A brighter portion indicates a higher OCT signal intensity. The SPUV image shows the SPUV per block (per 32×32 samples in this example). The LIV image shows the LIV for each observation point. A brighter portion indicates a larger LIV. According to this, the OCT image shows that the OCT intensity does not significantly change with the passage of time, while the SPUV image and the LIV image show that each of the SPUV and LIV significantly decreases with the passage of time. In particular, the decrease in the SPUV is significant from immediately after the end of culture (0 hr) to 4 hours after the end of culture (4 hr). This reflects the phenomenon that intracellular motion that was active immediately after the end of culture slows down over time.

Figure 12:
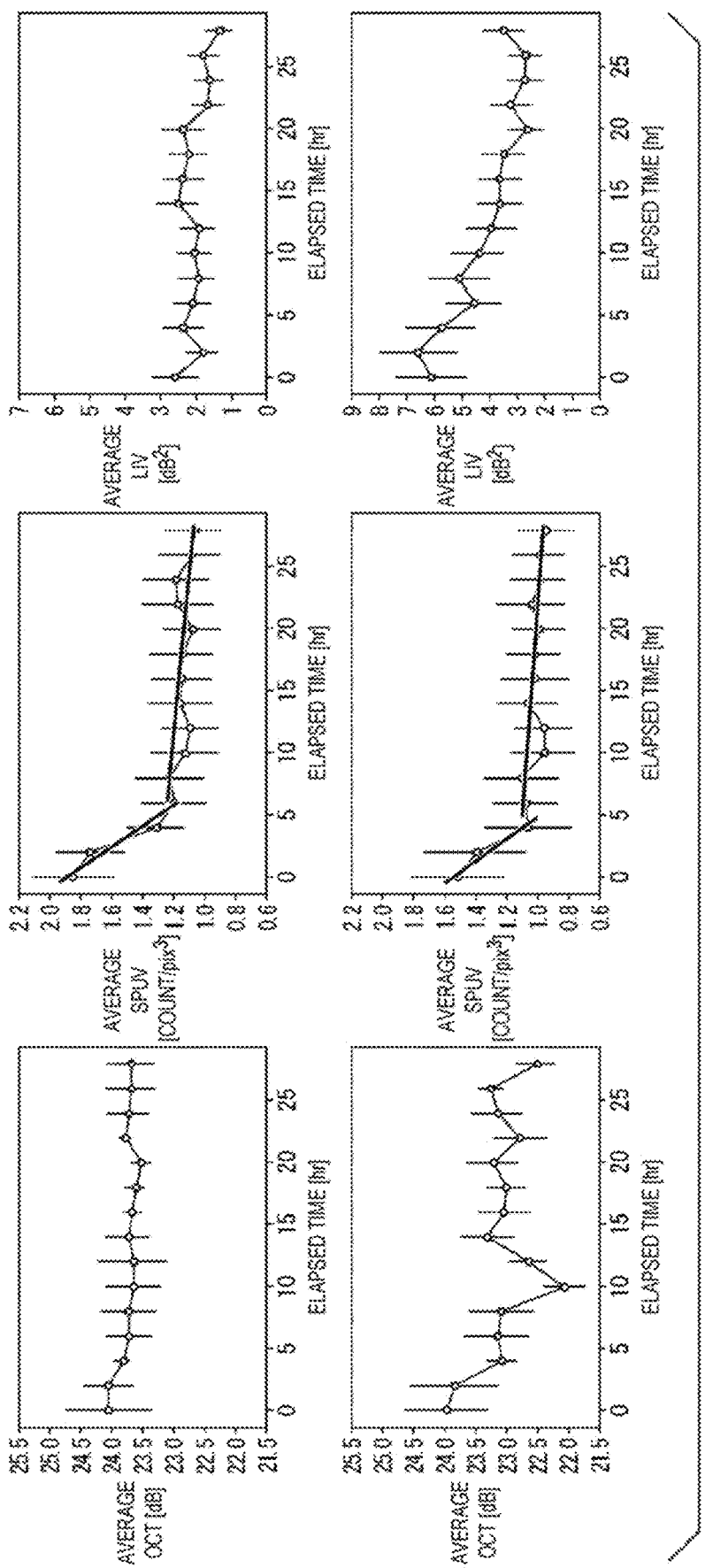
FIG. 12 is a diagram showing examples of change of each index value over time.

FIG. 12 is a diagram showing examples of change of each index value over time. In FIG. 12, the vertical axis indicates an average OCT intensity, an average SPUV, and an average LIV respectively in first, second, and third columns and the horizontal axis indicates time. In a first row, an observation target was a central portion of a biological sample. In a second row, a peripheral portion of a biological sample was observed. It was found that the average OCT intensity was stable in the central portion of the biological sample and had a tendency to fluctuate while decreasing over time in the peripheral portion. On the other hand, in each of the central portion and the peripheral portion of the biological sample, the average SPUV significantly decreased within 4 hours after the end of culture and the change thereafter became gradual. The average LIV shows a relatively constant downward trend over a 28 hour observation period. These facts indicate that the SPUV estimated from the OCT signal according to the present embodiment is more convenient than the OCT signal in observing cell activity. Further, the SPUV and LIV are thought to be able to observe activities involving different mechanisms of cells.

Although the above examples have been described with reference to the case where the x-direction resolution, the y-direction resolution, the SPUV, the SNR, and the ENS are mainly used as characteristic values, the present invention is not limited to this. A characteristic value set may include, for example, a mode of a wavefront aberration of the optical system and an aberration coefficient indicating the degree of the wavefront aberration. An aberration causes a phase change in the xy plane in a measurement signal and thus can be regarded as a factor that causes variations in the measurement signal. For example, Zernike coefficients $A_{nm}$ can be used as aberration coefficients. For example, the 0, 0-th Zernike coefficient $A_{00}$ is a coefficient indicating a constant term, the 1, 0-th Zernike coefficient $A_{10}$ is a coefficient indicating the degree of a gradient component in the x-direction, the 1, 1-th Zernike coefficient $A_{11}$ is a coefficient indicating the degree of a gradient component in the y-direction, the 2, 0-th Zernike coefficient $A_{20}$ is a coefficient indicating the degree of astigmatism in the 0° direction and the 90° direction, the 2, 1-th Zernike coefficient $A_{21}$ is a coefficient indicating the degree of a focus shift, the 2, 2-th Zernike coefficient $A_{22}$ is a coefficient indicating the degree of astigmatism in the 45° direction, the 3, 1-th Zernike coefficient $A_{31}$ is a coefficient indicating the degree of coma aberration of the x component, the 3, 2-th Zernike coefficients $A_{32}$ is a coefficient indicating the degree of coma aberration of the y component, and so on.

An aberration $W(f_x, f_y)$ with respect to a frequency $(f_x, f_y)$ in the two-dimensional plane xy when the incident direction of light is the z-direction is expressed by a Zernike polynomial shown in equation (6). In equation (6), ρ indicates a frequency in a radial direction from an optical axis directed in the z-direction and θ indicates a frequency in an azimuth direction. $R_n^{n-2m}(\rho)$ indicates an n, m-th order radial polynomial and is defined by equation (7). In equation (7), . . . ! indicates the factorial of an integer . . . n is an integer of 0 or more and m is an integer of 0 or more and n or less. The maximum order k is a predetermined integer of 0 or more. That is, the aberration $W(f_x, f_y)$ is given by the sum of products of the n, m-th Zernike coefficients $A_{nm}$, the n, n−2m-th order radial polynomials at that position, and cosine values cos|n−2m|θ (where n−2 m is 0 or more) or sine values sin|n−2m|θ (where n−2 m is less than 0).

[Math. 6]

$$W(x, y) = W(\rho\sin\theta, \rho\cos\theta) = $$
$$W(\rho, \theta) = \sum_{n=0}^{k}\sum_{m=0}^{n} A_{nm} \cdot R_n^{n-2m}(\rho) \cdot \begin{cases} \cos|n-2m|\theta, & (n-2m \geq 0) \\ \sin|n-2m|\theta, & (n-2m < 0) \end{cases} \quad (6)$$

[Math. 7]

$$R_n^{n-2m}(\rho) = \sum_{s=0}^{m}(-1)^s \frac{(n-s)!\rho^{n-2s}}{s!(m-s)!(n-m-s)!} \quad (7)$$

Therefore, when generating a measurement signal including the influence of aberrations, the training data generation unit 116 performs a two-dimensional Fourier transform in the xy plane on the three-dimensional point spread function PSF(x, y, z) to transform it into transform coefficients $p(f_x, f_y; z)$ in the frequency domain $(f_x, f_y)$. Then, the training data generation unit 116 performs a two-dimensional inverse Fourier transform in the $f_x$-$f_y$ plane on phase-changed transform coefficients, which are obtained by multiplying the transform coefficients $p(f_x, f_y; z)$ by a phase factor $e^{iaW(f_x, f_y)}$ indicating a phase change caused by an aberration, to calculate a point spread function PSF'(x, y, z) including phase changes due to aberrations in the three-dimensional spatial domain (x, y, z) as shown in equation (8). In equation (8), a is a predetermined real value indicating the degree of a phase change with respect to an aberration. $F_{fx, fz}^{-1}[\ldots]$ indicates the two-dimensional inverse Fourier transform of . . . in the $f_x$-$f_y$ plane.

$$PSF'(x,y,z) = F_{f_x,f_y}^{-1}[p(f_x,f_y,z) \cdot e^{iaW(f_x,f_y)}] \quad \text{[Math. 8]}$$

The training data generation unit 116 can generate an OCT speckle pattern O'(x, y, z) that has undergone phase changes due to aberrations as a measurement signal by convolving the above scatterer distribution f(x, y, z) with the PSF'(x, y, z) including aberrations.

Thus, by using a measurement signal that has undergone phase changes due to aberrations as an input value of training data, the training data generation unit 116 can calculate model parameters for calculating aberration coefficients as target values or model parameters for calculating other types of characteristic values as target values robustly to variations in aberration coefficients.

A characteristic value set may also include, for example, a dispersion coefficient relating to chromatic dispersion of the optical system. Chromatic dispersion causes a phase change with the wavelength in the z-direction in the measurement signal and thus can be regarded as a factor that causes variations in the measurement signal. In general, chromatic dispersion is caused by the frequency dependence of the propagation constant in the optical system. The propagation constant is a physical quantity corresponding to an effective wave number. When the propagation constant β(w) is Taylor-expanded with respect to the frequency ω around the center frequency Wo of the light source, it is expressed by equation (9).

[Math. 9]

$$\beta(\omega) = \beta(\omega_0) + a_1(\omega - \omega_0) + \frac{1}{2}a_2(\omega - \omega_0)^2 + \ldots \quad (9)$$

In equation (9), $\beta(\omega_0)$ indicates the propagation constant at the center frequency $\omega_0$ of incident light. $a_1$ and $a_2$ indicate the first derivative and the second derivative at the center frequency $\omega_0$, respectively. The first derivative $a_1$ corresponds to the reciprocal of the group velocity and the second derivative $a_2$ corresponds to group velocity dispersion. Thus, for example, the group velocity and group velocity dispersion can be used as dispersion coefficients.

Therefore, when generating a measurement signal including the influence of chromatic dispersion, the training data generation unit 116 performs a one-dimensional Fourier transform in the z-direction on the three-dimensional point spread function PSF(x, y, z) to transform it into transform coefficients q(ω; x, y) in the frequency domain (ω). Then, the training data generation unit 116 performs a one-dimensional inverse Fourier transform in the ω direction on phase-changed transform coefficients, which are obtained by multiplying the transform coefficients q(ω; x, y) by a phase factor $e^{ib\beta(\omega)}$ indicating a phase change due to chromatic dispersion, to calculate a point spread function PSF"(x, y, z) that has undergone phase changes due to chromatic dispersion in the three-dimensional spatial domain (x, y, z) as shown in equation (10). In equation (10), b is a predetermined real value indicating the degree of a phase change with respect to chromatic dispersion. $F_\omega^{-1}[\ldots]$ indicates the one-dimensional inverse Fourier transform of . . . in the ω direction.

[Math. 10]

$$PSF'''(x,y,z) = F_\omega^{-1}[q(\omega,x,y) \cdot e^{ib\beta(\omega)}] \quad (1)$$

The training data generation unit 116 can generate an OCT speckle pattern O"(x, y, z) that has undergone phase changes due to chromatic dispersion as a measurement signal by convolving the above scatterer distribution f(x, y, z) with the PSF"(x, y, z) including phase changes due to chromatic dispersion.

Thus, by using a measurement signal that has undergone phase changes due to chromatic dispersion as an input value of training data, the training data generation unit 116 can calculate model parameters for calculating dispersion coefficients as target values or model parameters for calculating other types of characteristic values as target values robustly to variations in dispersion coefficients.

A characteristic value set may include one or both of an aberration coefficient and a dispersion coefficient as dispersion coefficients.

Although the above description has been described with respect to the case where a measurement signal to be processed by the measurement signal processing device 100 is an OCT signal as an example, the present invention is not limited to this. The measurement signal can be applied to the present embodiment even if it is a signal indicating the state of a sample or a signal for analyzing the state of a sample using a measurement principle other than OCT. The measurement signal is not limited to a raw signal obtained by measurement or a signal generated by simulating the raw signal and may be a signal obtained by performing predetermined post-processing on such a signal or may be output display data whose main purpose is visualization such as, for example, an OCT image.

The measurement signal may be, for example, any of a speckle interference measurement signal, a photoacoustic measurement signal, or an ultrasonic tomography signal. A speckle interference measurement signal is a measurement signal obtained using a speckle interferometry method. The speckle interferometry method includes the step of irradiating a sample in a predetermined reference state with a coherent wave such as a laser beam as an incident wave and detecting an interference wave resulting from interference between a reflected wave from the sample and the incident wave which is a reference wave, the step of further detecting an interference wave generated by irradiating a sample whose state such as the position, direction, or shape has changed from the reference state through the same method, and the step of acquiring a speckle interference measurement signal indicating interference fringes obtained by interference between the detected interference wave and the reference wave. The speckle interference measurement signal is mainly used to analyze the amount of movement, a change in orientation, or the amount of deformation of the sample as a characteristic value. The incident wave is not limited to that of laser light which is visible light and may be that of X-rays, infrared light, an ultrasonic wave, or the like.

A photoacoustic measurement signal is a measurement signal acquired using a photoacoustic method. The photoacoustic method includes the step of irradiating a sample with laser light which is visible light or infrared light (including near-infrared light) as an incident wave and detecting a sound wave emitted from the sample as a photoacoustic measurement signal. Here, because molecules forming the sample absorb the incident wave and generate heat, an expansion of the sample due to the generated heat generates a sound wave. The photoacoustic measurement signal is used for a distribution of light absorbers included in the sample. Therefore, the photoacoustic measurement signal can be used to analyze, for example, the density of light absorbers or active portions of a sample as a characteristic value derived from the distribution of light absorbers. The generated sound wave is not limited to audible sound and may be an ultrasonic wave.

An ultrasound tomography signal is a measurement signal acquired using an ultrasound tomography method. The ultrasound tomography method includes the step of irradiating a sample with an ultrasonic wave as an incident wave and detecting an interference wave resulting from interference between the incident wave and a reflected wave emitted from the sample as an ultrasound tomography signal. The ultrasound tomography signal is used to analyze a characteristic value derived from the density, distribution, structure, or the like of tissues. The tomography method described above is not limited to a method using visible light or an ultrasonic wave as an incident wave and may use other types of waves such as infrared light, ultraviolet light, or X-rays.

As described above, the measurement signal processing device 100 according to the present embodiment includes the model learning unit 118 that determines a model parameter for calculating an estimated value for each of a plurality of training sets including a measurement signal and at least one type of predetermined characteristic value indicating characteristics of the measurement signal as a target value, with which a difference between the estimated value calculated for the measurement signal using a predetermined mathematical model and the target value is minimized. The measurement signal processing device 100 also includes the training data generation unit 116 that determines characteristic value sets, each being a set of a plurality of types of characteristic values indicating characteristics of a measurement signal including a target value, with which, for each target value, the target value is common to a plurality of characteristic value sets and generates, for each of the characteristic value sets, a training set including a measurement signal having characteristics indicated by the plurality of types of characteristic values and a target value. The measurement signal may be any of an OCT signal, a speckle interference measurement signal, a photoacoustic measurement signal, an ultrasonic tomography signal, or the like. A target value may include two or more types of characteristic values. In that case, model parameters for estimating two or more types of characteristic values can be generated from a measurement signal. Using the generated model parameters, two or more types of characteristic values can be estimated from a measurement signal with practical accuracy, which has been difficult or impossible in the related art. The two or more types of characteristic values may include, for example, a scatterer density and a resolution of the measurement system.

With this configuration, a measurement signal based on a plurality of types of characteristic values can be generated. With this measurement signal, for each characteristic value, the characteristic value is common to a plurality of training sets and model parameters can be determined to cause an estimated value calculated from the generated measurement signal to approximate a target value. Therefore, by using the determined model parameters, it is possible to calculate a target value from a measurement signal according to the mathematical model robustly to variations in the characteristic values of types different from the target value. For example, if the characteristic value is the scatterer density of the sample and the parameters of the plurality of types of characteristic values include the intensity or the signal-to-noise ratio of the measurement signal, then the scatterer density of the sample can be estimated independently of variations in the intensity or the signal-to-noise ratio. The cell nucleus density of a biological tissue sample, which is an example of the scatterer density, can be estimated more correctly using a measurement signal. Thus, it is possible to reduce wrong decisions or load of human decisions in pathological research and diagnosis.

The training data generation unit 116 may determine a tissue structure (for example, a tissue structure in which scatterers are distributed at a scatterer density that has been set) of a sample to be measured based on at least one of the plurality of types of characteristic values (for example, the scatterer density) and generate a measurement signal for a wave incident on the sample based on the determined tissue structure.

With this configuration, a measurement signal is generated based on a tissue structure determined using a characteristic value that has been set and thus it is possible to generate various measurement signals by quantitatively indicating characteristics of tissue structures which are under different conditions.

The training data generation unit 116 may determine a characteristic value within a predetermined value range for each of the plurality of types using a random number. With this configuration, a plurality of types of characteristic values that are randomly distributed can be efficiently generated over a large number of characteristic value sets. Also, biases of the distributions of the plurality of types of characteristic values can be reduced compared to those of a plurality of types of characteristic values determined by humans. Therefore, it is possible to obtain model parameters that enable a target value to be calculated with higher accuracy.

Also, the plurality of types of characteristic values may include a spatial resolution, an aberration coefficient, or a dispersion coefficient relating to chromatic dispersion in the measurement system of a sample. Thus, it is possible to reduce or eliminate deterioration in the accuracy of characteristic value estimation due to variations in the spatial resolution, aberration coefficient, or chromatic dispersion which depend on the measurement system itself or the sample to be measured.

The mathematical model includes a neural network including an input layer that outputs a signal value for each observation point of the measurement signal, which has been input to the input layer, to a first intermediate layer, a plurality of intermediate layers, and an output layer that outputs an estimated value based on an output value received from a last intermediate layer. The plurality of intermediate layers may be formed by repeatedly stacking one or more convolutional layers, each of which outputs an arithmetic value obtained by performing convolution processing on an input value received from an immediately preceding layer to a next layer, a plurality of times. With this configuration, features contributing to variations of a target value are extracted from an input measurement signal each time a layer is stacked and thus the estimation accuracy of the target value can be improved. One or more final layers including the output layer may be fully connected layers, each of which outputs arithmetic values obtained by performing convolution processing on all of a plurality of input values received from an immediately preceding layer using a smaller number of parameter sets than the number of the input values. Thus, components significantly affecting a characteristic value which are given from an immediately preceding layer can be fully taken into account and the degree of freedom can be reduced to finally derive the characteristic value.

The measurement signal processing device 100 may include the characteristic estimation unit 120 that calculates, for the measurement signal, an estimated value for the target value based on the mathematical model using the model parameters. With this configuration, an estimated value for a target value can be calculated with high accuracy from an input measurement signal using the model parameters acquired by the device.

Although the embodiments of the present invention have been described in detail with reference to the drawings, the specific configurations are not limited to those described above and various design changes or the like can be made without departing from the gist of the present invention.

For example, the measurement signal processing device 100 may be implemented as a part of the OCT system 1 or may be a single device independent of the optical system. In that case, the measurement system control unit 112 may be omitted from the control unit 110 of the measurement signal processing device 100. The measurement signal acquisition unit 114 may acquire a measurement signal from another device such as a data storage device or a PC, without being limited to the optical system.

The measurement signal processing device 100 may include the display unit 150 and the operation unit 160, one or both of which may be omitted.

One or both of the characteristic estimation unit 120 and the output processing unit 122 may be omitted from the measurement signal processing device 100. When the characteristic estimation unit 120 is omitted, the model learning unit 118 may output the calculated model parameters to another device such as a data storage device, a PC, or another measurement signal processing device. The output destination device may have the same function as the characteristic estimation unit 120, that is, the function of calculating a characteristic value according to a predetermined mathematical model using model parameters obtained from the measurement signal processing device 100 for the measurement signal.

Although the above description illustrates that the training data generation unit 116 generates, as information indicating a tissue structure, a scatterer distribution f(x, y, z) indicating a state in which scatterers are stochastically and randomly distributed in the observation area at a scatterer density given as a characteristic value, the present invention is not limited to this. The training data generation unit 116 may acquire tissue structure information indicating a tissue structure of a sample from another device and the tissue structure information may include a plurality of tissue structures and known characteristic values indicating characteristics (such as, for example, an SPUV and an ENS) of the tissue structures. In the case where the tissue structure information is acquired, the training data generation unit 116 does not need to determine the tissue structure of the sample and the tissue structures and characteristic values may be used as a part of a characteristic value set. A tissue structure may be one in which scatterers are regularly arranged within the observation area, for example, a lattice in which scatterers are arranged spatially at predetermined intervals. The scattering intensity or the scattering cross section of each scatterer may be included in a characteristic value set as a characteristic value relating to the tissue structure.

Although the case of using a CNN as a mathematical model has been described as an example, the present invention is not limited to this. The mathematical model may be other types of neural networks such as, for example, a recurrent neural network or a probabilistic neural network. Other types of mathematical models such as, for example, a random forest and a multiple regression model may be used as long as the relationship between a measurement signal and a target value can be obtained. The multiple regression model is suitable if the relationship between a measurement signal as an input value and a target value as an output value is linear or can be approximated linearly.

The activation function in the CNN is not limited to a rectified linear unit and may be any of a sigmoid function, a softmax function, or the like. The model error index is not limited to an MSE and may be cross entropy or the like.

A part or the entirety of the measurement signal processing device 100 in the above embodiment may be implemented as an integrated circuit such as a large scale integration (LSI). Functional blocks of the measurement signal processing device 100 may be individually implemented as processors or some or all of the functional blocks may be integrated and implemented as a processor. The circuit integration is not limited to LSI and may be implemented by a dedicated circuit or a general-purpose processor. If an integrated circuit technology that replaces LSI emerges with the progress of semiconductor technology, an integrated circuit according to the technology may be used.

REFERENCE SIGNS LIST

1 OCT system
10 Light source
20 Beam splitter
30a, 30b, 50a, and 50b Collimator
40 Reference mirror
60a, 60b Galvano mirror
70 Spectrometer
100 Measurement signal processing device
110 Control unit
112 Measurement system control unit
114 Measurement signal acquisition unit
116 Training data generation unit
118 Model learning unit
120 Characteristic estimation unit
122 Output processing unit
130 Storage unit
140 Input/output unit
150 Display unit
160 Operation unit

The invention claimed is:

1. A measurement signal processing device comprising:
a memory; and
a processor connected to the memory and that:
determines a model parameter for calculating an estimated value for each of a plurality of training sets, each including a measurement signal and at least one type of predetermined characteristic value indicating characteristics of the measurement signal as a target value, to minimize a difference between the estimated value calculated for the measurement signal using a predetermined mathematical model and the target value;
determines characteristic value sets, each being a set of a plurality of types of characteristic values indicating characteristics of the measurement signal, each including the target value, such that, for each target value, the target value is common to a plurality of characteristic value sets; and
generates, for each of the characteristic value sets, each of the plurality of training sets including the target value and a measurement signal having characteristics indicated by the plurality of types of characteristic values, wherein
the target value includes a scatterer density of a sample, and
the plurality of types of characteristic values include an intensity of a signal-to-noise ratio of the measurement signal.

2. The measurement signal processing device according to claim 1, wherein the training data generation circuitry is configured to determine a tissue structure of a sample to be measured based on at least one of the plurality of types of characteristic values, and generate the measurement signal for a wave incident on the sample based on the tissue structure.

3. The measurement signal processing device according to claim 1, wherein the training data generation circuitry is configured to determine a characteristic value within a predetermined value range for each of the plurality of types using a random number.

4. The measurement signal processing device according to claim 1, wherein the training data generation circuitry is configured to determine a tissue structure of the sample in which scatterers are distributed at the scatterer density.

5. The measurement signal processing device according to claim 1, wherein the target value further includes a spatial resolution of a measurement system.

6. The measurement signal processing device according to claim 1, wherein
the mathematical model includes a neural network including an input layer that outputs a signal value for each observation point of the measurement signal, which has been input to the input layer, to a first intermediate layer, a plurality of intermediate layers, and an output layer that outputs an estimated value based on an output value received from a last intermediate layer,
the plurality of intermediate layers are formed by repeatedly stacking one or more convolutional layers, each of which outputs an arithmetic value obtained by performing convolution processing on an input value received from an immediately preceding layer to a next layer, a plurality of times, and
one or more final layers including the output layer are fully connected layers, each of which outputs arithmetic values obtained by performing convolution processing on all of a plurality of input values received from an immediately preceding layer using a smaller number of parameter sets than the number of the input values.

7. The measurement signal processing device according to claim 1, further comprising a characteristic estimation circuitry configured to calculate, for the measurement signal, an estimated value for the target value based on the mathematical model using the model parameter.

8. The measurement signal processing device according to claim 7, further comprising an output processing circuitry,
wherein the measurement signal indicates a signal value for each observation point,
the characteristic estimation circuitry is configured to calculate the estimated value for each block including a plurality of observation points, and
the output processing circuitry is configured to transform the estimated value into a pixel value and output display data indicating the pixel value to a display unit.

9. The measurement signal processing device according to claim 1, wherein the measurement signal is any of an optical coherence tomography measurement signal, a speckle interference measurement signal, a photoacoustic measurement signal, or an ultrasonic tomography signal.

10. A measurement signal processing method for a measurement signal processing device, the method comprising:
a model learning step of determining a model parameter for calculating an estimated value for each of a plurality of training sets, each including a measurement signal and at least one type of predetermined characteristic value indicating characteristics of the measurement signal as a target value, to minimize a difference between the estimated value calculated for the measurement signal using a predetermined mathematical model and the target value; and
a training data generation step of
determining characteristic value sets, each being a set of a plurality of types of characteristic values indicating characteristics of the measurement signal, each including the target value, such that, for each target value, the target value is common to a plurality of characteristic value sets and
generating, for each of the characteristic value sets, each of the plurality of training sets including the target value and a measurement signal having characteristics indicated by the plurality of types of characteristic values, wherein
the target value includes a scatterer density of a sample, and
the plurality of types of characteristic values include an intensity or a signal-to-noise ratio of the measurement signal.

11. A computer program product stored in a non-transitory computer-readable medium that is programmed to perform:
a model learning process of determining a model parameter for calculating an estimated value for each of a plurality of training sets, each including a measurement signal and at least one type of predetermined characteristic value indicating characteristics of the measurement signal as a target value, to minimize a difference between the estimated value calculated for the measurement signal using a predetermined mathematical model and the target value; and
a training data generation process of
determining characteristic value sets, each being a set of a plurality of types of characteristic values indicating characteristics of the measurement signal, each including the target value, such that, for each target value, the target value is common to a plurality of characteristic value sets and
generating, for each of the characteristic value sets, each of the plurality of training sets including the target value and a measurement signal having characteristics indicated by the plurality of types of characteristic values, wherein
the target value includes a scatterer density of a sample, and
the plurality of types of characteristic values include an intensity or a signal-to-noise ratio of the measurement signal.

12. A measurement signal processing device comprising:
a memory; and
a processor connected to the memory and that:
determines a model parameter for calculating an estimated value for each of a plurality of training sets, each including a measurement signal and at least one type of predetermined characteristic value indicating characteristics of the measurement signal as a target value, to minimize a difference between the estimated value calculated for the measurement signal using a predetermined mathematical model and the target value;
determines characteristic value sets, each being a set of a plurality of types of characteristic values indicating characteristics of the measurement signal, each including the target value, such that, for each target value, the target value is common to a plurality of characteristic value sets; and
generates, for each of the characteristic value sets, each of the plurality of training sets including the target value and a measurement signal having characteristics indicated by the plurality of types of characteristic values, wherein
the plurality of types of characteristic values include a spatial resolution, an aberration coefficient, or a dispersion coefficient relating to chromatic dispersion in a measurement system.

13. A measurement signal processing method for a measurement signal processing device, the method comprising:
a model learning step of determining a model parameter for calculating an estimated value for each of a plurality of training sets, each including a measurement signal and at least one type of predetermined characteristic value indicating characteristics of the measurement signal as a target value, to minimize a difference between the estimated value calculated for the measurement signal using a predetermined mathematical model and the target value; and
a training data generation step of
determining characteristic value sets, each being a set of a plurality of types of characteristic values indicating characteristics of the measurement signal, each including the target value, such that, for each target value, the target value is common to a plurality of characteristic value sets, and
generating, for each of the characteristic value sets, each of the plurality of training sets including the target value and a measurement signal having characteristics indicated by the plurality of types of characteristic values, wherein
the plurality of types of characteristic values include a spatial resolution, an aberration coefficient, or a dispersion coefficient relating to chromatic dispersion in a measurement system.

14. A computer program product stored in a non-transitory computer-readable medium that is programmed to perform:
- a model learning process of determining a model parameter for calculating an estimated value for each of a plurality of training sets, each including a measurement signal and at least one type of predetermined characteristic value indicating characteristics of the measurement signal as a target value, to minimize a difference between the estimated value calculated for the measurement signal using a predetermined mathematical model and the target value; and
- a training data generation process of
- determining characteristic value sets, each being a set of a plurality of types of characteristic values indicating characteristics of the measurement signal, each including the target value, such that, for each target value, the target value is common to a plurality of characteristic value sets, and
- generating, for each of the characteristic value sets, each of the plurality of training sets including the target value and a measurement signal having characteristics indicated by the plurality of types of characteristic values, wherein
- the plurality of types of characteristic values include a spatial resolution, an aberration coefficient, or a dispersion coefficient relating to chromatic dispersion in a measurement system.

* * * * *